United States Patent
Morrissey et al.

(10) Patent No.: US 8,172,803 B2
(45) Date of Patent: May 8, 2012

(54) CANNULA INSERTION DEVICE

(75) Inventors: Ray Morrissey, Cambridge (GB);
Steven McLellan, London (GB); Barry Lillis, London (GB)

(73) Assignee: Applied Medical Technology Ltd (GB)

( * ) Notice: Subject to any disclaimer, the term of this patent is extended or adjusted under 35 U.S.C. 154(b) by 0 days.

(21) Appl. No.: 12/667,855

(22) PCT Filed: Jun. 30, 2008

(86) PCT No.: PCT/GB2008/050519
§ 371 (c)(1),
(2), (4) Date: Mar. 3, 2010

(87) PCT Pub. No.: WO2009/007742
PCT Pub. Date: Jan. 15, 2009

(65) Prior Publication Data
US 2010/0204652 A1    Aug. 12, 2010

(30) Foreign Application Priority Data
Jul. 6, 2007  (GB) .................... 0713136.0

(51) Int. Cl.
*A61M 5/178* (2006.01)
*A61M 5/00* (2006.01)

(52) U.S. Cl. ............. 604/164.08; 604/110; 604/164.01; 604/164.04; 604/263

(58) Field of Classification Search ............... 604/93.01, 604/110, 164.01–164.08, 174–180, 263
See application file for complete search history.

(56) References Cited

U.S. PATENT DOCUMENTS

| | | | |
|---|---|---|---|
| 5,522,803 A | 6/1996 | Teissen-Simony | |
| 6,488,663 B1 * | 12/2002 | Steg | 604/164.08 |
| 6,520,938 B1 * | 2/2003 | Funderburk et al. | 604/164.08 |
| 6,942,652 B1 * | 9/2005 | Pressly et al. | 604/508 |
| 7,220,241 B2 * | 5/2007 | Csincsura et al. | 604/93.01 |
| 7,220,242 B2 * | 5/2007 | Putter et al. | 604/93.01 |
| 7,270,649 B2 * | 9/2007 | Fitzgerald | 604/164.01 |
| 7,585,287 B2 * | 9/2009 | Bresina et al. | 604/93.01 |
| 7,867,199 B2 * | 1/2011 | Mogensen et al. | 604/164.04 |
| 2004/0158207 A1 | 8/2004 | Hunn et al. | |
| 2005/0245874 A1 * | 11/2005 | Carrez et al. | 604/160 |
| 2005/0283114 A1 * | 12/2005 | Bresina et al. | 604/93.01 |
| 2006/0015071 A1 | 1/2006 | Fitzgerald | |
| 2006/0030815 A1 | 2/2006 | Csincsura et al. | |
| 2006/0161108 A1 * | 7/2006 | Mogensen et al. | 604/164.01 |

(Continued)

FOREIGN PATENT DOCUMENTS

EP    0 453 264 A1    4/1991

(Continued)

*Primary Examiner* — Victoria P Campbell
(74) *Attorney, Agent, or Firm* — Stroock & Stroock & Lavan LLP

(57) ABSTRACT

A cannula insertion device comprises an elongate frame (4) and a hub (5) mounted to the frame and arranged to be slidably moveable from a first position forwards along a longitudinal axis to a second position relative to the frame and a needle (11) projecting forwards from the hub and carrying a detachable cannula (2) assembly including a cannula. The frame and hub are arranged to allow the hub to be moved forwards from the first position to the second position so as to insert the cannula into a patient and to be drawn backwards to a withdrawn position. The needle is shielded by the frame when the hub is in the first position and also when in the withdrawn position.

13 Claims, 23 Drawing Sheets

U.S. PATENT DOCUMENTS

| | | | |
|---|---|---|---|
| 2006/0184104 A1* | 8/2006 | Cheney et al. | 604/93.01 |
| 2007/0191771 A1* | 8/2007 | Moyer | 604/158 |
| 2007/0270754 A1* | 11/2007 | Soderholm et al. | 604/164.08 |

FOREIGN PATENT DOCUMENTS

| | | |
|---|---|---|
| EP | 1 776 980 A1 | 4/2007 |
| FR | 2 867 082 A1 | 9/2005 |
| FR | 2 884 723 A1 | 10/2006 |
| WO | WO 90/11103 | 10/1990 |
| WO | WO 97/36636 | 10/1997 |
| WO | WO 00/56388 | 9/2000 |
| WO | WO 02/07804 A1 | 1/2002 |
| WO | WO 2005/092411 A1 | 10/2005 |
| WO | WO 2006/062636 A1 | 6/2006 |
| WO | WO 2007/098771 A2 | 9/2007 |

* cited by examiner

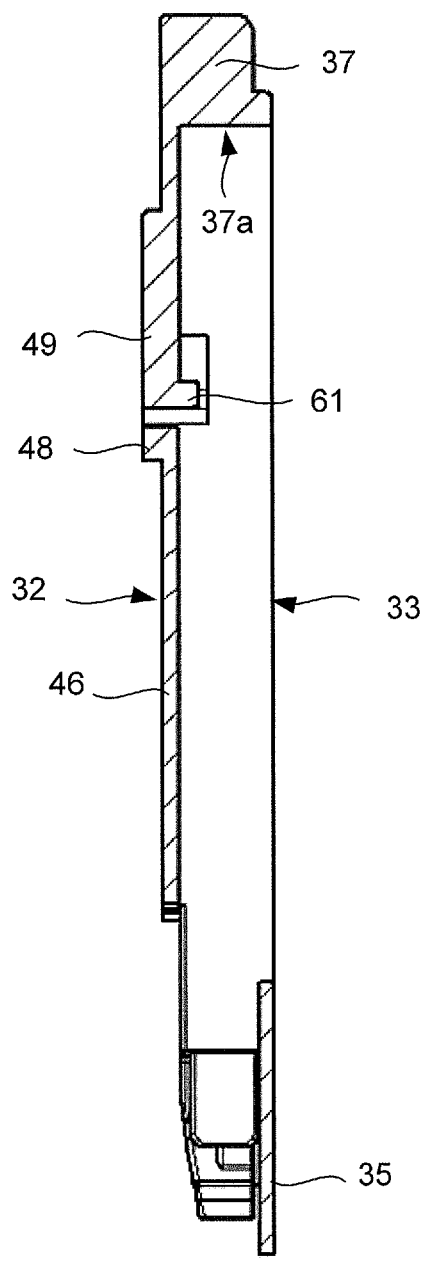
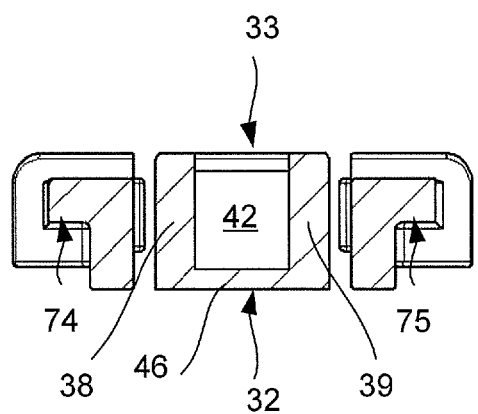
Fig. 8
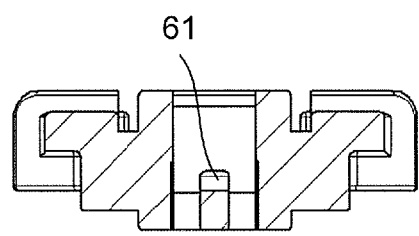
Fig. 9
Fig. 7

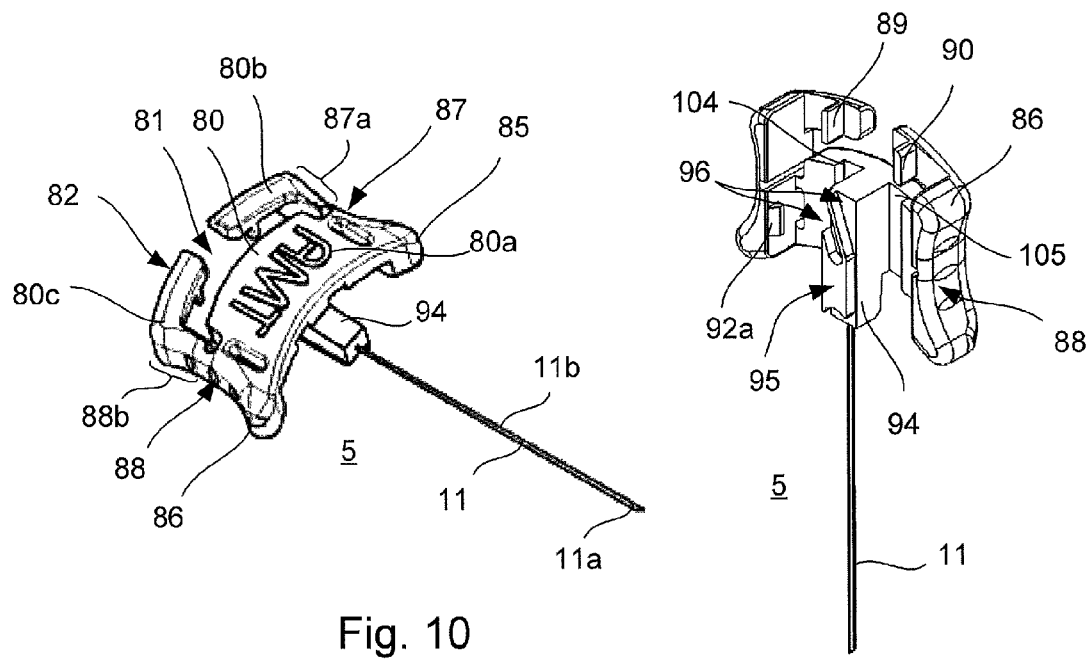
Fig. 10
Fig. 11
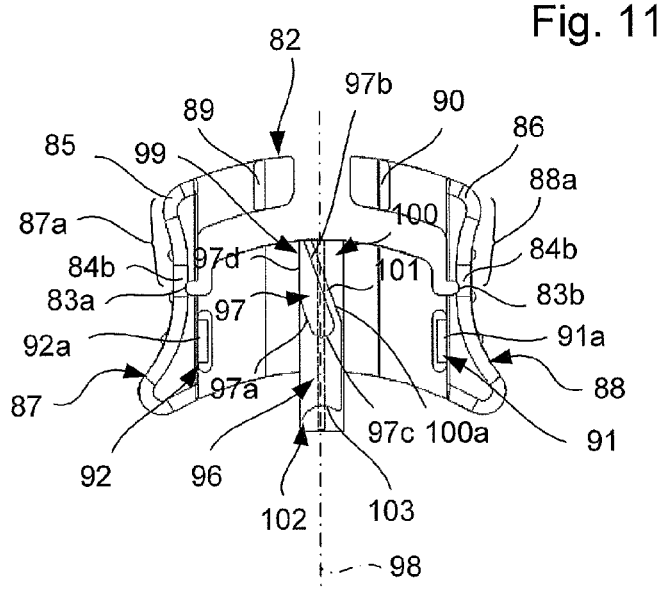
Fig. 12

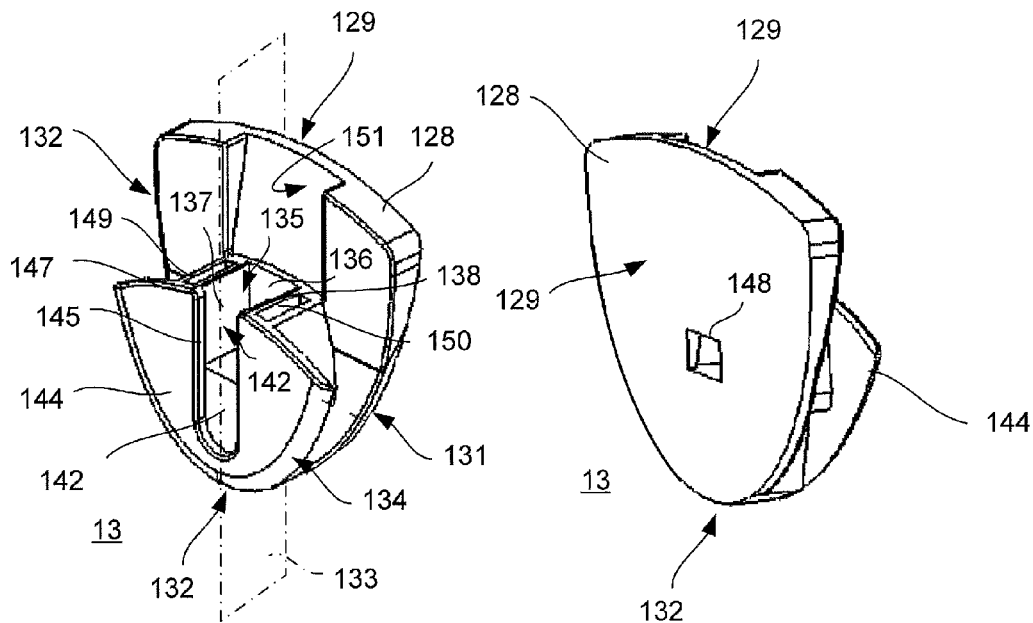
Fig. 15  Fig. 16
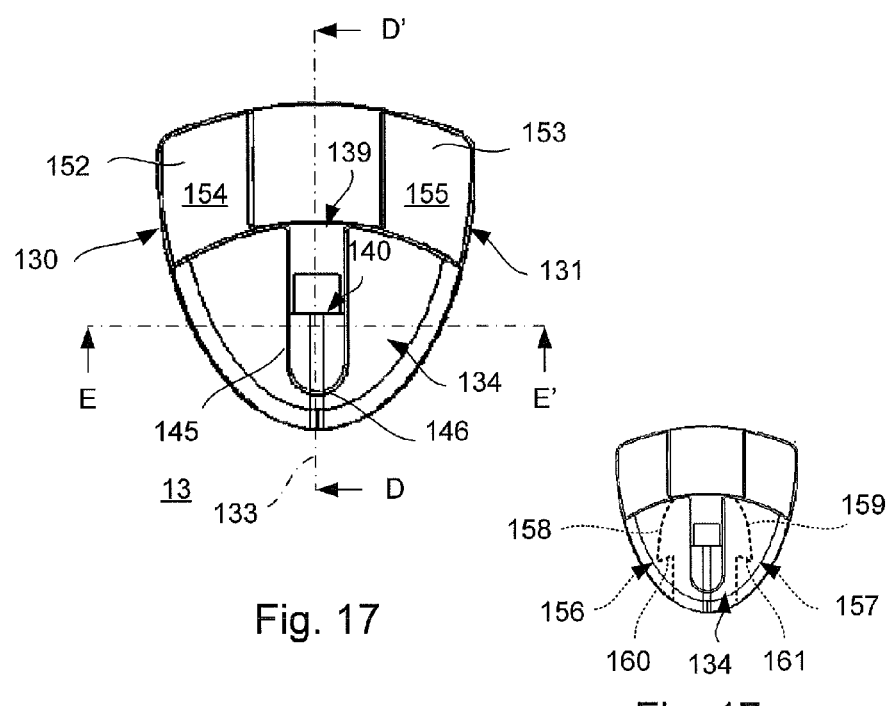
Fig. 17
Fig. 17a

CANNULA INSERTION DEVICE

CROSS-REFERENCE TO PRIOR APPLICATIONS

This application is the U.S. National Phase application under 35 U.S.C. §371 of International Application No. PCT/GB2008/50519, filed on Jun. 30, 2008, which claims the benefit of Great Britain Patent Application No. 0713136.0, filed on Jul. 6, 2007, all of which are incorporated by reference herein.

FIELD OF THE INVENTION

The present invention relates to a cannula insertion device.
The present invention also relates to a connector for connecting a tube to an infusion device.

BACKGROUND

Treatment of some medical conditions involves administering a drug (or a combination of drugs) subcutaneously or intravenously into a patient.

A drug delivery system can be divided in two parts, namely a device for supplying the drug (such as a bag, pump or syringe) and a tubing arrangement for delivering the drug into the patient.

The tubing arrangement includes a soft cannula, which can also be referred to as a catheter. One end of the cannula is inserted into the patient, leaving the other end available for connection to the drug-supplying device. The cannula is held in place by taping the cannula to the surface of the skin of the patient or by using a housing which itself is attached to the surface of the skin.

To insert the cannula into the patient, a device is used which employs an introducer needle, for example as described in U.S. Pat. No. 5,522,803. The cannula is carried on the needle such that, when the needle pierces the skin and underlying tissue, the cannula is also inserted. The needle is then withdrawn, leaving the cannula in place.

Existing insertion devices suffer the drawback that the needle is often exposed before and/or after insertion, thereby allowing possible contamination of the needle and exposing the operator to so-called "needle stick" injury, which carries with it a risk of infection.

The present invention seeks to provide an improved cannula insertion device which reduces the possibility of injury.

In the prior art arrangement described in U.S. Pat. No. 5,522,803, once the cannula has been inserted into the patient, the inserter needle is withdrawn by disconnecting an inserter hub from the cannula housing and attaching a connecting hub in its place. The connecting hub includes a hollow needle which pierces a membrane (or "septum") in the cannula housing.

However, the prior art connecting hub suffers at least two drawbacks. Firstly, the hollow needle on the connecting hub is itself a potential hazard and could lead to needle stick injury. Secondly, the connecting hub can be difficult to align and orientate with the cannula housing.

The present invention seeks to ameliorate one or both of these problems.

The prior art arrangement described in U.S. Pat. No. 5,522,803 does not describe how ancillary medication can be delivered through the same access site. One possible solution is to disconnect the tubing, insert a needle through the septum and inject. However, this arrangement only allows one fluid to be delivered at a time. Another solution is to provide a multi-port device upstream. However, this can be inconvenient for the patient since such a device can restrict mobility. Moreover, the line between the cannula housing and multi-port device may need to be flushed. The longer the line, the greater the amount of fluid required for flushing. Furthermore, the arrangement requires additional connectors.

The present invention seeks to ameliorate at least one of these problems.

SUMMARY OF THE INVENTION

According to a first aspect of the present invention there is provided a cannula insertion device comprising a frame, a hub mounted to the frame and arranged to be slidably moveable from a first position to a second position in a first direction and a needle projecting in the first direction from the hub and carrying a detachable assembly including a cannula, the needle being shielded by the frame when the hub is in the first position, the frame and hub arranged to allow the hub to be moved from the first position to the second position in the first direction so as to insert the cannula into a patient and to be moved in a second, reverse direction to a third position in which the frame shields the needle. Thus, the needle is shielded before and after it is inserted which can help to minimise possible contamination and needle stick injury.

To help make the device easier to handle using two hands, the frame may be elongate and the hub may be slidably moveable along the longitudinal axis of the frame.

The first position may lie between the second and third positions.

The frame and hub may be further arranged to provide a latching means so as to lock the hub in the third position so as to prevent the hub being moved in the first direction. This can help to minimise further the possibility of needle stick injury.

The frame may include first and second beams running adjacently between first and second ends, the hub and frame arranged such that the needle sits between the beams. The frame may include a cover spanning the beams and running between the first and second ends so as to define a space in which the needle sits. This can help to limit access to the cannula and needle and so reduce further possible contamination and needle stick injury.

The first and second beams may include respective lip portions partially spanning the beams and running between the first and second ends so as to define a slot along the frame. This can help to limit access to the cannula and needle and so reduce further possible contamination and needle stick injury.

The frame may include first and second arms running along opposite sides of a central portion of the frame and attached thereto by respective deformable hinges, distal ends of the arms arranged to provide jaws for releasably attaching the device to a housing for receiving the detachable assembly. The hub may have opposing surfaces for gripping between a finger and thumb of one hand and which lie outside the arms of the frame, at least a portion of the hub being deformable so as to allow the opposing surfaces to be moved inwards when pressed together. The hub may include first and second arms disposed either side of a central portion and said opposing surfaces may be outer surfaces of the first and second arms.

The frame may be arranged such that when the hub is substantially in the third position and the opposing surfaces are pressed together, posterior distal ends of the arms of the frame are pressed inwards and the anterior distal ends of the arms of the frame move outwards away from the central portion. Thus, if the device is attached to a housing for receiving the detachable assembly, the device can be released from the housing only when the needle is safely withdrawn.

The frame and hub may be provided with cooperating surfaces such that when the hub is in a position which allow posterior distal ends of the arms of the frame to be pressed inwards, the surfaces resist inward movement of the posterior distal ends of the arms of the frame and thus prevent outward movement of anterior distal ends of the arms of the frame away from the central portion.

The cooperating surface of the frame may comprise outward facing sides of the central portion and the cooperating surface of the hub may comprise upstanding fins.

The frame and hub may be arranged such that when the hub is between the first and second positions and when the opposing surfaces of the hub are pressed together, anterior distal ends of the arms are pressed towards the central portion.

According to a second aspect of the present invention there is also provided apparatus comprising the cannula insertion device and a housing for receiving the detachable cannula assembly, the device removeably attached to the housing.

The device may be detachable from the housing only once the hub is in the third position. Thus, the device can be released from the housing only when the needle is safely withdrawn.

The apparatus may comprise a tube connector for attaching to the housing in place of the cannula insertion device.

According to a third aspect of the present invention there is also provided a method of inserting a cannula using a cannula insertion device comprising an frame, a hub mounted to the frame and arranged to be slidably movable from a first position in a first direction to a second position relative to the frame along the frame and a needle projecting forwards from the hub in the first direction and carrying a detachable cannula assembly including a cannula, the needle being shielded by the frame when the hub is in the first position, the method comprising moving the hub in the first direction from the first position to the second position so as to insert the cannula into a patient and moving the hub in a second, reverse direction to a third position in which the frame shields the needle.

According to a fourth aspect of the present invention there is provided a connector for connecting a tube to an infusion device comprising a base portion, a hollow needle projecting from the base portion in a given direction and having a shaft and a tip and a spatulate member projecting from the base portion parallel to the needle and fully facing the shaft of the needle, the spatulate member arranged to extend beyond the tip of the needle and further arranged so as to be furthest extent of the connector in said given direction. Thus, the spatulate member not only provides a guard for limiting access to one side of the needle, but also can serve as an index for orientating and guiding the connector into the infusion device.

According to a fifth aspect of the present invention there is provided a tube connector for connecting a tube to an infusion device comprising a first coupling means of a first type arranged to cooperate with a coupling means of a second type on the infusion device so as to couple the connector to the infusion device, a second coupling means of the second type arranged to cooperate with coupling means of the first type on another connector. Thus, the tube connector can provide 'Y'-piece having substantially the same coupling means as the infusion device and so reduce the number of types of connector needed.

The first and second coupling means may be arranged substantially in line.

The first coupling means may comprise a pair of opposing clips and the second coupling means comprises a pair of retaining members.

The first coupling means may be arranged in a forward section of the connector and the second coupling means may be arranged in a rear section of the connection.

The tube connector may comprise a hollow needle, a passage having a first end which feeds into a lumen of the hollow needle and second end capped by a septum; and a port for receiving a tube and which feeds into the passage between the first and second ends. The port may be arranged to receive the tube transversely to a line between the first and second coupling means. The port may be directed away from a plane in which the first and second coupling means lie.

The port may be arranged to receive a tube substantially parallel to a line between the first and second coupling means, for example, by providing an T-shaped bend. This can help to minimise the profile of the tube connector.

According to a sixth aspect of the present invention there is provided a tube connector and another tube connector removeably insertable into to the tube connector. The tube connector and other tube connector need not be identical. For example, the other tube connector may not include coupling means of the second type.

According to a seventh aspect of the present invention there is provided an infusion set comprising an infusion device and a tube connector removeably insertable into to the infusion device.

DESCRIPTION OF THE DRAWINGS

Embodiments of the present invention will now be described, by way of example, with reference to the accompanying drawings in which:

FIG. 7 is longitudinal cross sectional view of the chassis shown in FIG. 4 taken along the line A-A';

FIG. 8 is transverse cross sectional view of the chassis shown in FIG. 4 taken along the line B-B';

FIG. 9 is transverse cross sectional view of the chassis shown in FIG. 4 taken along the line C-C';

FIG. 10 is a top perspective view of a slider of a cannula insertion device;

FIG. 11 is a bottom perspective view of a slider of a cannula insertion device;

FIG. 12 is a bottom plan view of a slider of a cannula insertion device;

FIG. 15 is a perspective view of a septum housing;

FIG. 16 is another perspective view of a septum housing;

FIG. 17 is a plan view of a septum housing;

FIG. 17a is plan view of the septum housing shown in FIG. 17;

DETAILED DESCRIPTION OF EMBODIMENTS OF THE INVENTION

Figure 1:
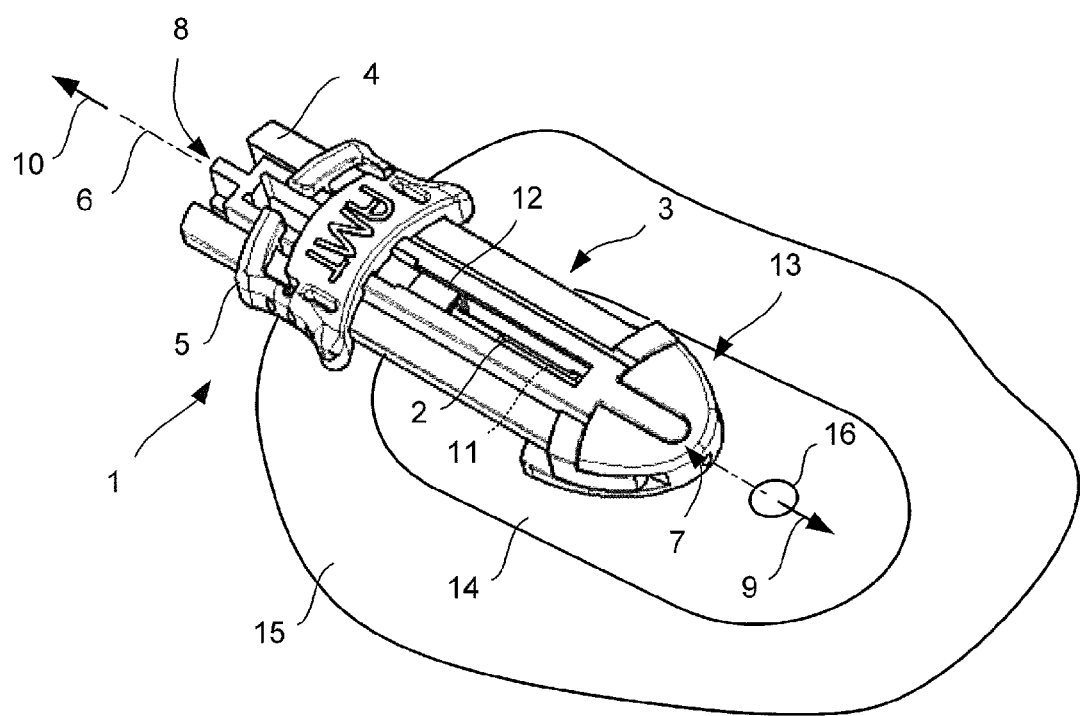
FIG. 1 is a top perspective view of an embodiment of apparatus for inserting a cannula into a patient and, once inserted, holding it in place according to the present invention.

Referring to FIG. 1, an assembly 1 for inserting a soft cannula 2 or "catheter" into a patient and, once inserted, holding it in place in accordance with the present invention is shown. The assembly 1 includes a device 3 for inserting the cannula (hereinafter referred to as the "insertion device") having an elongate frame 4 (hereinafter referred to as the "chassis") and a hub 5 slidably moveable along the chassis 4. The hub 5 is hereinafter referred to as the "slider".

The slider 5 travels along a longitudinal axis 6 running between first and second ends 7, 8 of the chassis 4 in first and second directions 9, 10. During normal use, the first and second directions 9, 10 are usually forwards (towards the patient's skin) and backwards respectively and so these terms will be used hereinafter.

A needle 11 projects forwardly from the slider 5 and carries, on its shaft 11b (FIG. 10), a detachable sub-assembly 12 (hereinafter referred to as the "septum assembly") which includes the soft cannula 2.

The assembly 1 also includes a housing 13 for receiving the septum assembly 12. The septum housing 13 is attached to an upper side of an adhesive pad 14 which can be used to fix it to the surface 15 of the skin of a patient. The adhesive pad 14 has a clear area 16 through which the cannula 2 and needle 11 may pass and which allows a clear view of the point of insertion of the cannula 2 into the skin 15.

The assembly 1 is used to insert the soft cannula 2 subcutaneously under the surface 15 of the skin. Once the soft cannula 2 is inserted, the two main parts of the assembly 1, namely the cannula insertion device 3 and the septum housing 13, can be separated. A connector 21 (FIG. 2e) or a multi-way adapter or 'Y'-piece connector 23 (FIG. 2f) can be coupled to the septum housing 13 in place of the insertion device 3 so as to deliver a drug, a combination of drugs or other fluid by infusion. For example, the drug may be insulin for the treatment of diabetes.

Referring to FIGS. 2a to 2f, the apparatus 1 is shown in different states prior to and during use. For clarity, the adhesive pad 14 (FIG. 1) is not shown.

Figure 2:
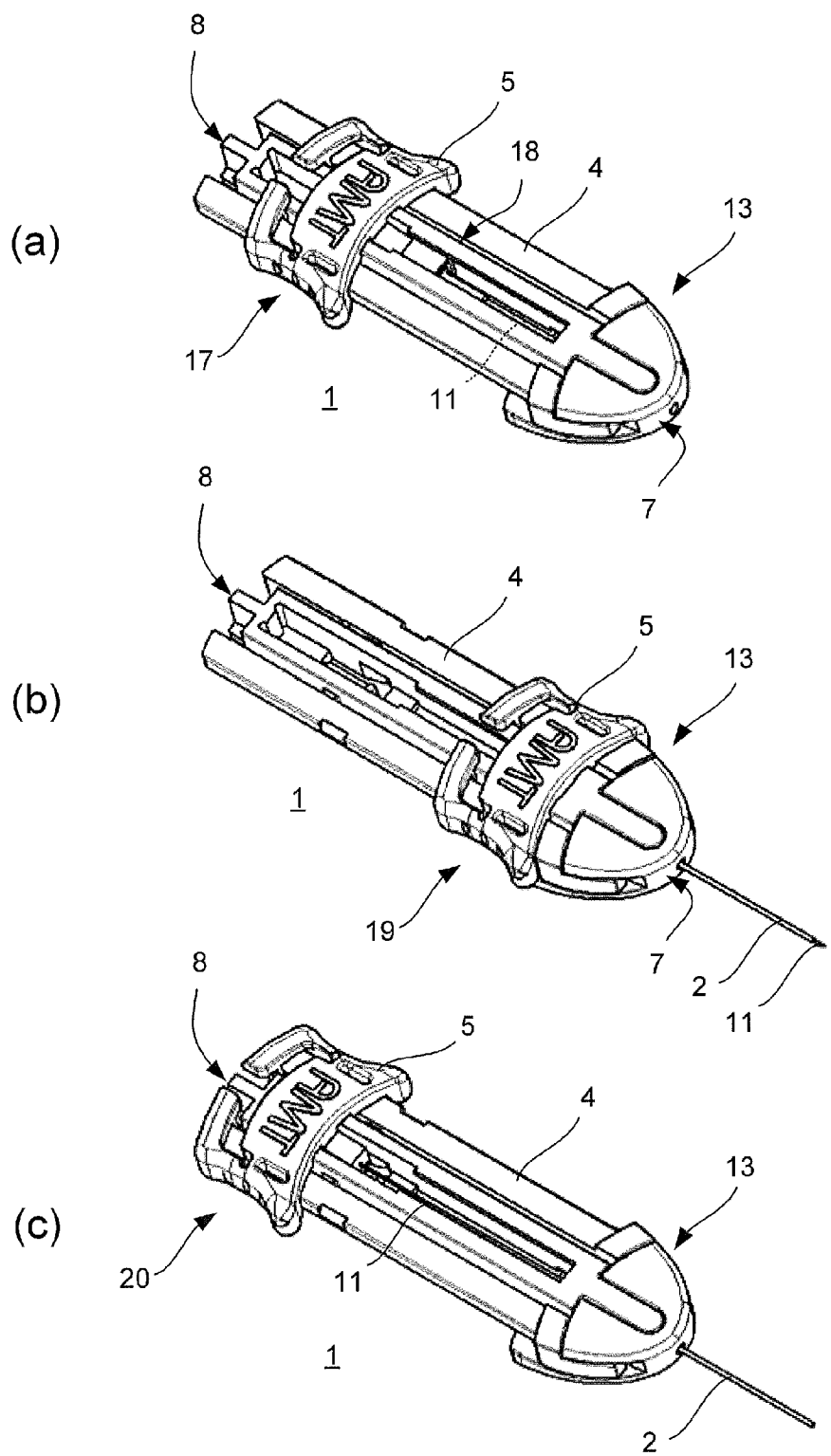
FIGS. 2a to 2d are top perspective views of the apparatus shown in FIG. 1 at different stages during use.
FIG. 2e is a top perspective view of a septum housing and a tube connector.
FIG. 2f is a top perspective view of a septum housing and a 'Y'-piece tube connector.
Figure 2:
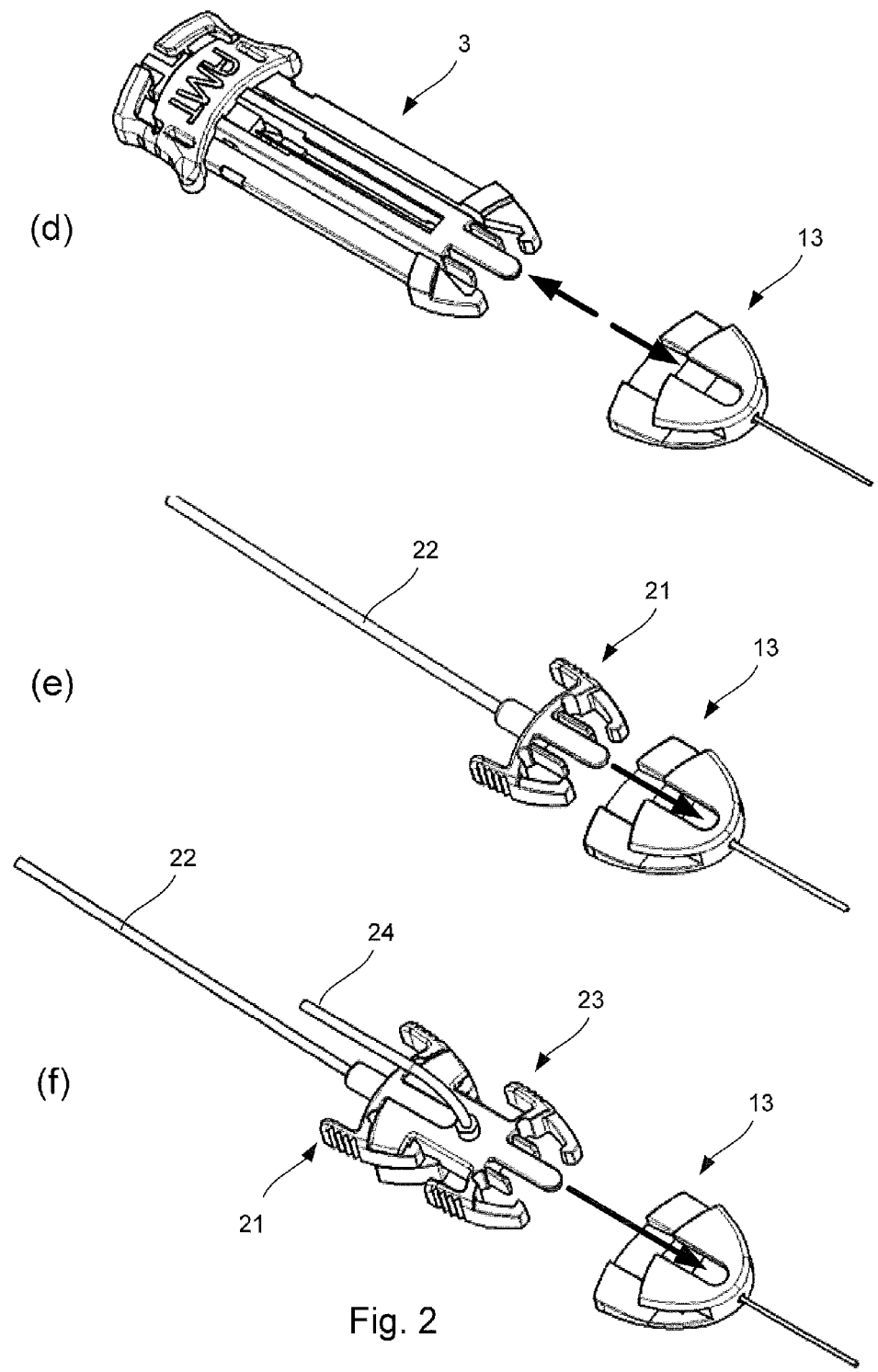

FIG. 2a shows the assembly 1 in an as-supplied and ready-to-use state. In this state, the slider 5 is located in a first position 17 between the rear end 8 and a mid-point 18 between the front and rear ends 7, 8 of chassis 4. In this position, the needle 11 is shielded by the chassis 4. Thus, the chassis 4 helps to avoid potential contamination of the needle 11 and protects an operator from possible needle stick injury.

FIG. 2b shows the assembly 1 during use, once the slider 5 has been pushed into a second position 19 near the front end 7 of the chassis 4. In this position, the septum assembly 12 (not shown in FIG. 2b) is seated in the septum housing 13. The needle 11 and soft cannula 2 project forwardly from the septum housing 13 into tissue of the patient (not shown).

FIG. 2c shows the assembly 1 during use, after the slider 5 has been drawn back into a third position 20 near the rear end 8 of the chassis 4. In this position, the septum assembly 12 (not shown in FIG. 2c) is retained in the septum housing 13 and the soft cannula 2 still projects forwardly from the septum housing 13. However, the needle 11 is withdrawn, back within the chassis 4.

As will be explained in more detail later, in normal operation, the insertion device 3 cannot be detached from the septum housing 13 when the slider 5 is in the first position 17. Moreover, the slider 5 cannot be drawn back directly to the third position 20. In normal operation, the insertion device 3 can only be detached from the septum housing 13 once the slider 5 has travelled forwards from the first position 17 to the second position 19 and then been drawn back to the third position 20. The slider 5 is locked in the third position 20 to prevent the used needle 11 being used again or being exposed inadvertently.

FIG. 2d shows the insertion device 3 once it has been detached from the septum housing 13.

Referring to FIG. 2e, once the insertion device 3 (FIG. 2d) has been detached, a tube connector 21 can be attached to the septum housing 13. The tube connector 21 supplies a drug (or other fluid) from a drug-supplying device, such as a pump (not shown), via a tube 22.

Referring to FIG. 2f, a 'Y'-piece connector 23 may be attached to the septum housing 13. The 'Y'-piece connector 23 may be used to supply another drug from another drug supplying device (not shown), such as a syringe, via another tube 24. The tube connector 21 can be attached to the 'Y'-piece 23, thus allowing drugs to be supplied simultaneously to the same access site via separate lines 22, 24.

Referring to FIGS. 3 to 14, the insertion device 3 will now be described in more detail.

Referring in particular to FIGS. 3 to 9, the chassis 4 is moulded as a single piece and is formed from a plastic, such as polypropylene. The chassis 4 is generally flat in side view and rectangular in plan view and is sufficiently small and light that an operator can hold it comfortably between their finger and thumb of one hand. In this example, the chassis 4 has a length of about 65 mm, a width of about 20 mm and a thickness of about 7 mm.

The chassis 4 comprises an elongate central body 25 and first and second arms 26, 27 running along opposite outward facing sides 28, 29 of the central body 25 between front and rear ends 7, 8 of the chassis 4. The body 25 and the arms 26, 27 are integrally formed and joined by respective flexible hinges 30, 31 between the rear 8 and middle 18 of the chassis 4.

The chassis 4 has a first face 32 (FIG. 4) and a second face 33. During normal use, the first face 32 (FIG. 4) is usually placed on or directed to the skin and so is hereinafter referred to as the bottom face 32. The second face 33 is hereinafter referred to as the top face 33.

On the top face 33, the central body 25 includes a flat, elongate rectangular hollow panel or frame 34 having first and second long side sections 34a, 34b. An elongate spatulate member 35, e.g. a member which is long and is broader than it is thicker, projects forwardly from the base frame 34. As will be explained in more detail later, the spatulate member 35 provides a dorsal guard to shield the tip of the needle 11 (FIG. 10) and can also serve as an index for guiding the insertion device 3 (FIG. 1) into the septum housing 13 (FIG. 1).

The frame 34 serves as a top side to the central body 25 which has an elongate 'Y'-shaped body member 36 having a short stem 37 and forwardly projecting parallel arms 38, 39 (hereinafter referred to as "beams") extending towards the bottom face 32 from the long side sections 34a, 34b of the base panel 34. The beams 38, 39 provide rails on which the slider 5 (FIG. 1) can travel.

Inward facing sides 40, 41 of the beams 38, 39 define a space or lumen 42 in which the needle 11 (FIG. 10) sits and travels. The lumen 42 has a front open end 43 through which the needle 11 (FIG. 10) projects. Tabs 44, 45 which are flat and narrow in section project forwardly from each respective beams 38, 39 to provide lateral guards to shield the needle 11 (FIG. 10).

Outward facing sides 28, 29 of the beams 38, 39 (i.e. of the central body 25) provide stopping surfaces for co-operating with corresponding depending fins 89, 90 (FIG. 11) on the slider 5 so as to prevent opposing gripping surfaces 87, 88 (FIG. 10) of the slider 5 being pressed together when the slider 5 is forwards of the third position 20 (FIG. 2c).

Figure 4:
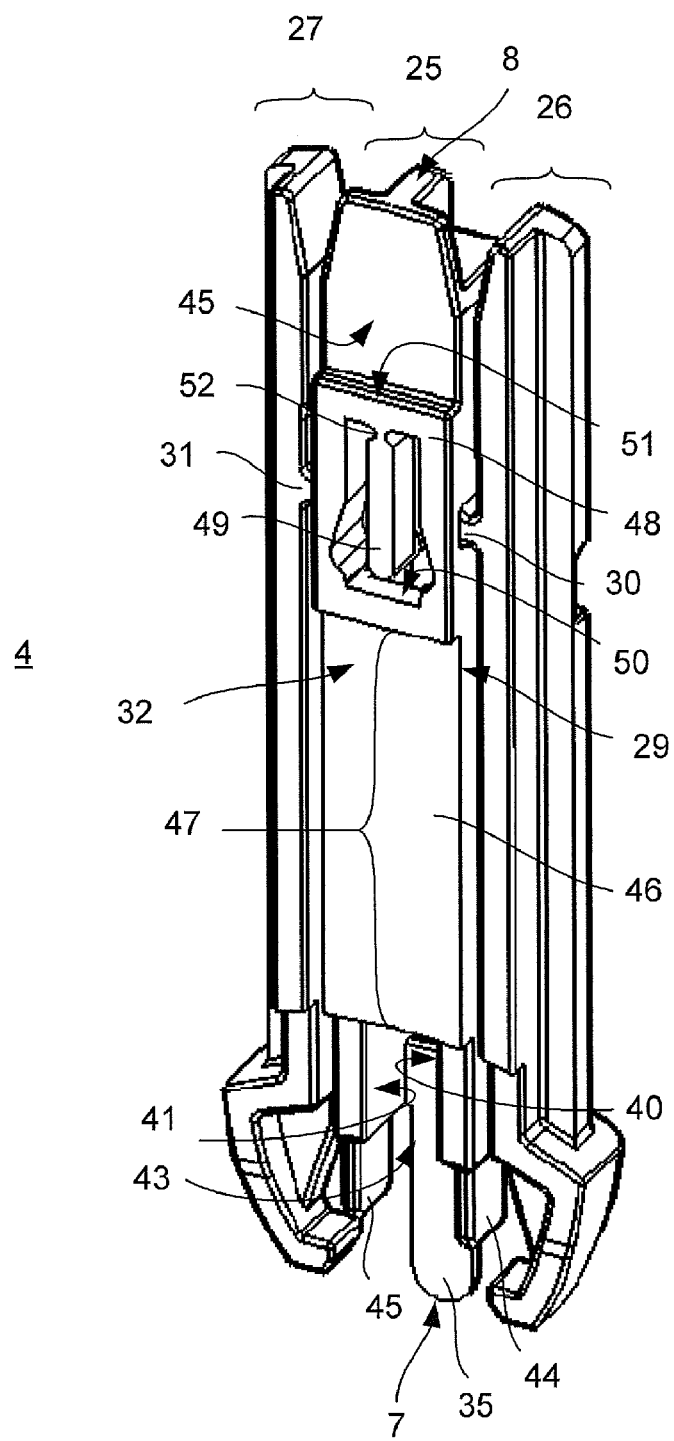
FIG. 4 is another perspective view of a chassis of a cannula insertion device.

Referring in particular to FIG. 4, on the bottom face 32, the central body 25 includes a panel 46 bridging the beams 38, 39 along a mid section 47 of the body 25. The panel 46 helps to limit access to the lumen 42 defined between the beams 38, 39.

Figure 5:
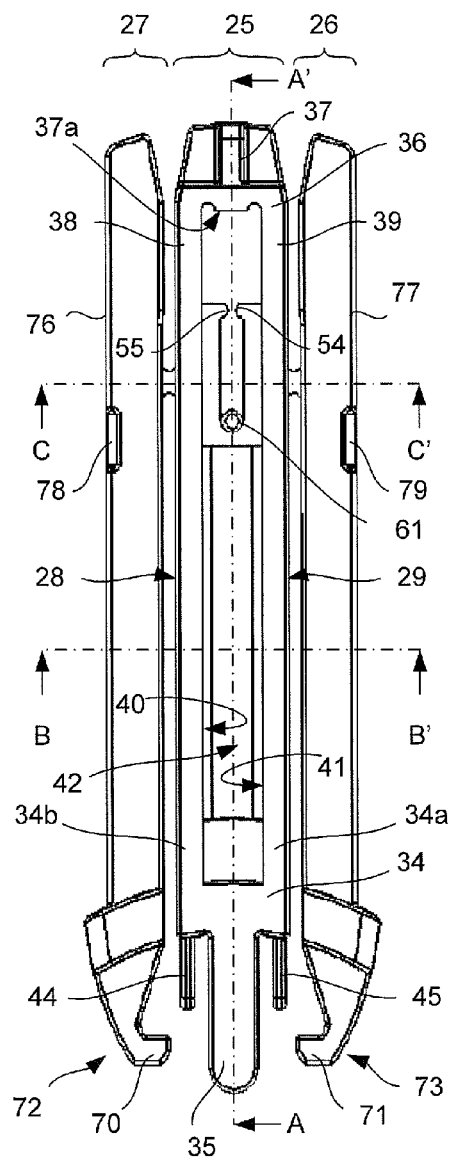
FIG. 5 is a bottom plan view of a chassis of a cannula insertion device.
Figure 6:
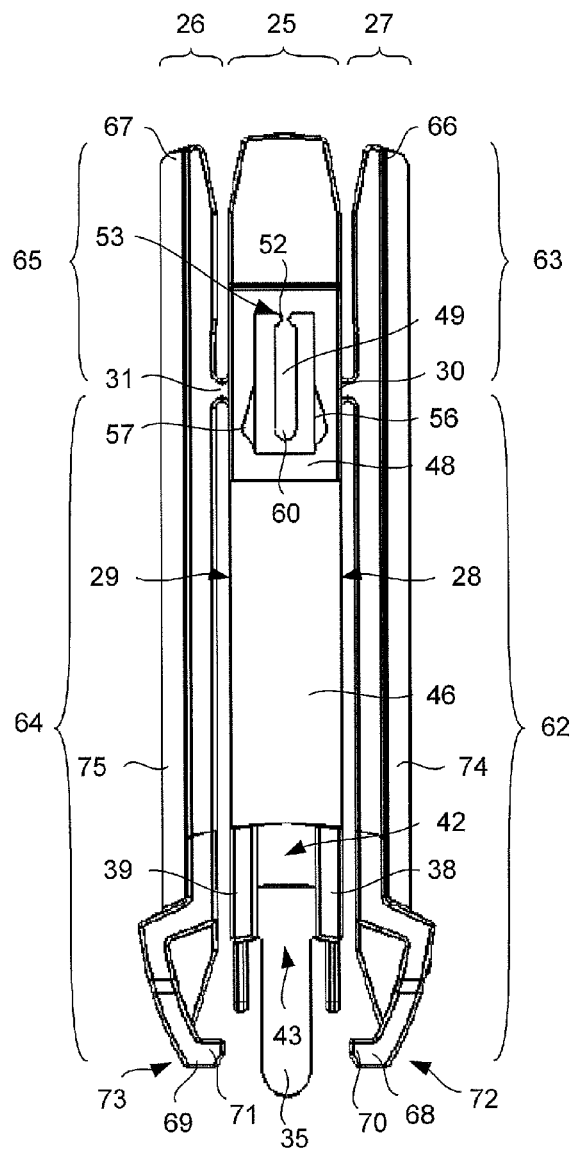
FIG. 6 is a top plan view of a chassis of a cannula insertion device.

Referring in particular to FIGS. 5 and 6, also on the bottom face 32, the central body 25 includes a smaller rectangular frame 48 which houses a finger 49. The finger 49 is joined to an inside wall 50 of the smaller frame 48 at a rear end 51 by a flexible joint 52 so as to allow the finger 49 to pivot laterally. The flexible joint 52 is provided by the finger 49 at its base 53, where it meets frame 48, by a pair of notches 54, 55 on opposite sides of finger so as to provide a narrow, waist portion. The inside wall 50 includes recesses 56, 57 on its sides portions 58, 59 to accommodate the finger 49 when fully deflected, i.e. pivoted. A distal end 60 of the finger 49 carries a depending pin or peg 61. The finger 49 and peg 61 form a part of a latch assembly for limiting movement of the slider 5.

The central body 25 provides a box-shaped, cage-like structure having an open end through which the needle 11 (FIG. 10) can travel. Guards arranged on three sides of the open end to protect the needle 11 (FIG. 10) in ready-to-use and used states. It will be appreciated that other, differently shaped, cage-like structures can be used.

As explained earlier, the arms 26, 27 run along opposite outward facing sides 28, 29 of the central body 25 between the front and rear ends 7, 8 of the chassis 4. The arms 26, 27 are joined to the body 25 by respective deformable pivots 30, 31.

Referring in particular to FIGS. 5 and 6, the pivots 30, 31 divide the arms 26, 27 into forward and rear sections 62, 63, 64, 65. Pressing together the arms 26, 27 in the rear section 64, 65, for example at rear distal ends 66, 67, causes forward distal ends 68, 69 of the arms 26, 27 to move outwards, away from the central body 25.

Figure 19:
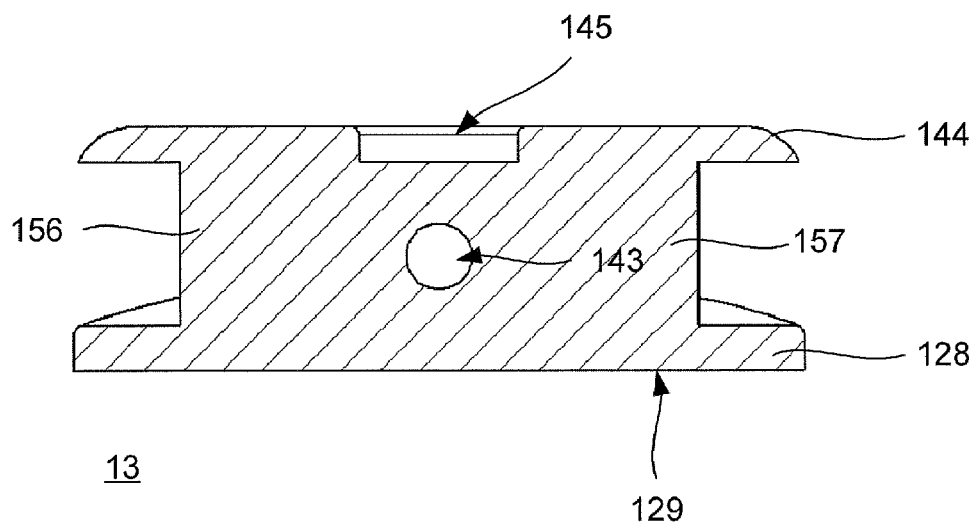
FIG. 19 is a cross sectional view of the septum housing shown in FIG. 17 taken along the line E-E'.

The forward distal ends 68, 69 of the arms 26, 27 each have inwardly facing barbed heads 70, 71 to provide clips 72, 73 for co-operating with clip retaining members 156, 157 (FIG. 19) in the septum housing 13.

As shown in FIGS. 8 and 9, the arms 26, 27 generally have the shape of an inverted 'L' in cross section. An upper portion 74, 75 of each arms forms a lip or ridge running down each arm and provides a clip retaining member for co-operating with a clip 91, 92 (FIG. 12) on the slider 5 (FIG. 12) to hold the chassis 4 and slider 5 (FIG. 12) together.

Figure 3:
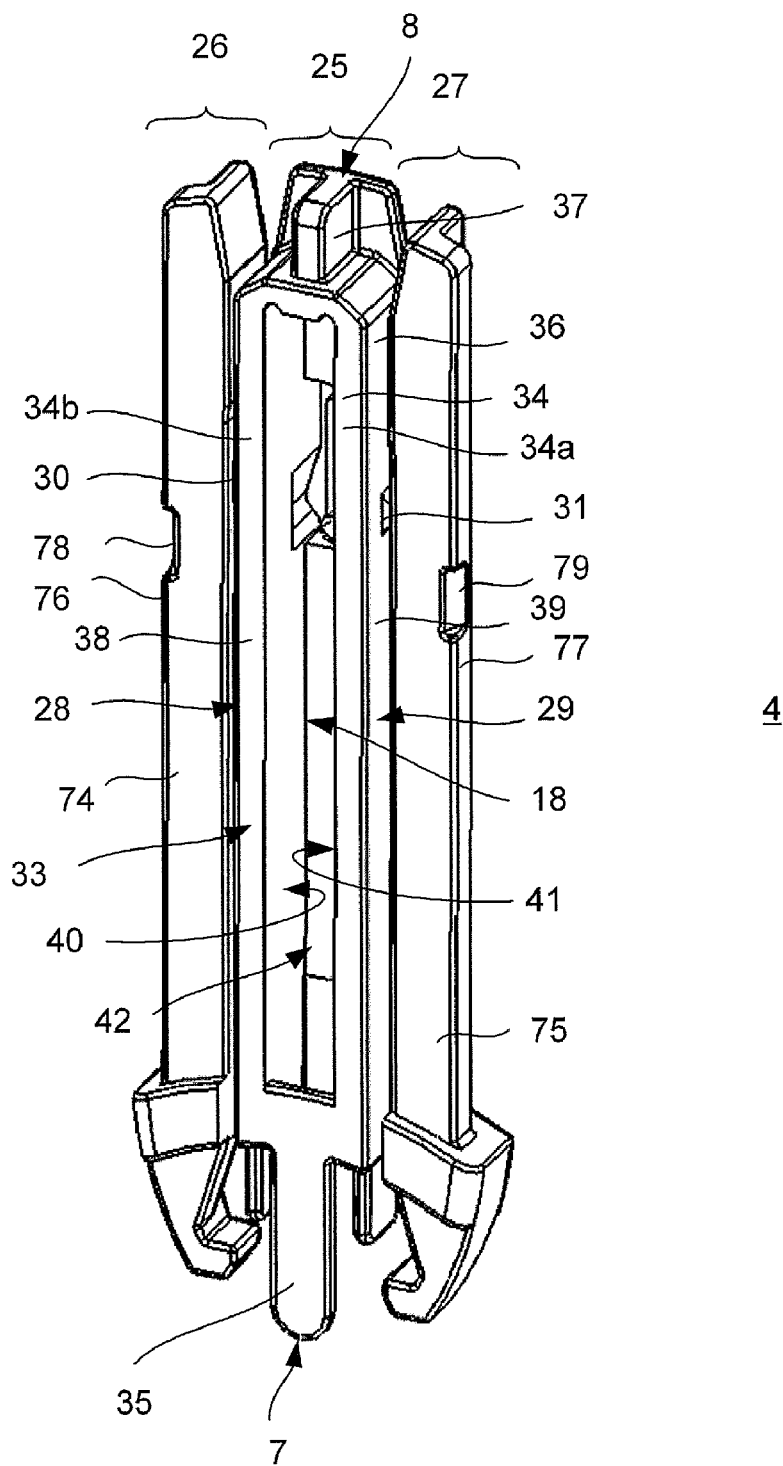
FIG. 3 is a perspective view of a chassis of a cannula insertion device.

Referring in particular to FIG. 3, an upper outside edge 76, 77 of each upper portion 74, 75 has a chamfered portion 78, 79 to provide downward sloping leading edges to help clip the slider 5 (FIG. 11) onto the chassis 4 during assembly.

Referring now to FIGS. 10, 11 and 12, the slider 5 is moulded in a single piece and is formed from a plastic, such as polypropylene. The slider 5 is generally flat and roof-like so as to lie across the top of the chassis 4 (FIG. 3) and to hang down over the arms 26, 27 (FIG. 3) of the chassis 4 (FIG. 3) so as to provide surfaces for gripping between a finger and thumb of one hand. For example, the slider 5 has a length (without the needle 11) of about 20 mm, a width of about 25 mm and a thickness of about 7 mm.

The slider 5 includes a panel 80 having a shallow 'Y'-shaped slot 81 extending forwardly from a rear edge 82 of the panel 80 to form a main portion 80a and first and second arm portions 80b, 80c which extend backwards and then inwards from the main portion 80a.

Referring in particular to FIG. 12, notches 83a, 83b are provided to form flexible hinges 84a, 84b between the main portion 80a and the arm portions 80b, 80c. The panel 80 includes depending lateral edge portions 85, 86 having opposing outer surfaces 87, 88 for gripping between a finger and thumb of one hand. The opposing outer surfaces 87, 88 are ribbed to help improve grip.

Referring in particular to FIG. 12, rear portions 87a, 88b of the opposing outer surfaces 87, 88 (i.e. rearward of the flexible hinges 84a, 84b) can be pressed towards each other. However, each arm portion 80b, 80c has a depending fin 89, 90 which provides a stop for co-operating with a respective one of the sides 28, 29 (FIG. 3) of the beams 26, 27 (FIG. 3) so as to prevent the rear portions 85a, 85b of the outer surfaces 87, 88 being pressed towards each other when the slider 5 is not located at the third position 20 (FIG. 2c).

Referring in particular to FIGS. 11 and 12, inward pointing barbed heads portions 91a, 92a are provided on the lateral edge portions 85, 86 to provide clips 91, 92 for co-operating with ridge portions 74, 75 of the arms 26, 27 and so allow the slider 5 to be clipped onto the chassis 4.

An elongate block 94 depends from an underside face 95 of the main panel portion 80a. The block 94 is arranged such that when the chassis 4 and slider 5 are coupled together, the block 94 sits in the lumen 42 (FIG. 3).

A stainless steel needle 11 (FIG. 10) projects forwardly from the block 94. The needle 11 includes a shaft 11a (FIG. 10) and a tip 11b (FIG. 10). The needle 11 has a length of about 35 mm and an outer diameter of 0.4 mm. The needle 11 is fixed either by over moulding or gluing into the block 94.

A downward face 95 of the block 94 is recessed so as to provide a path 96 for guiding the peg 61 (FIG. 5) so as to provide another part of the latch assembly for limiting movement of the slider 5.

The path 96 includes a linear close-ended groove 97 obliquely angled with respect to an axis 98 along which the slider 5 travels. The groove 97 has first and second sides 97a, 97b, a closed end 97c and an open end 97d. The open end 97d emerges from a generally rear facing corner 99 of the block 94. The path 96 includes and open sided recess 100 having a wall 101 obliquely angled with respect to the axis of travel 98 and extending from the rear facing corner 99 and across the block 94. As shown in FIG. 12, the wall 101 defines one side 97a of the groove 97. The wall 101 also defines a side 100a of the recess 100. The wall 101 curves around to the front of the block 94. The wall 101 defines a front-facing end 102 which is made concave so as to define a detent 103.

The underside face 95 of the main panel portion 80a is recessed to provide grooves 104, 105 for receiving the beams 38, 39 (FIG. 3).

Figure 13:
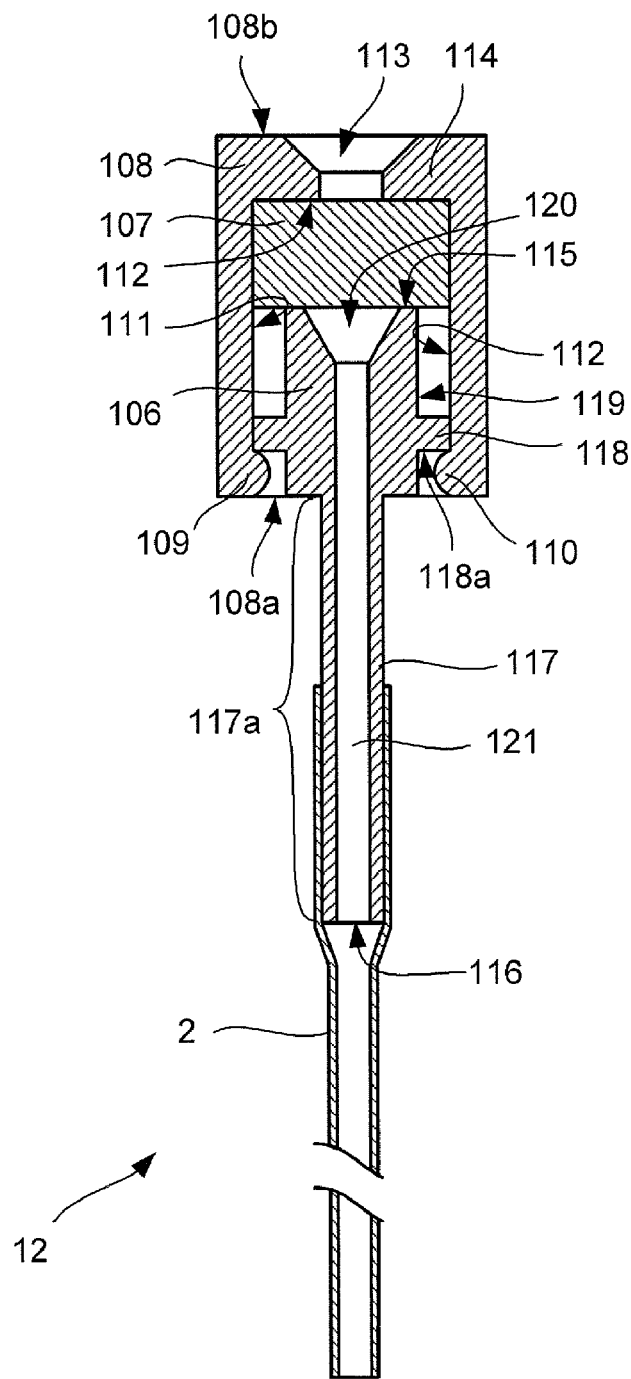
FIG. 13 is a longitudinal cross-sectional view of a septum assembly.
Figure 14:
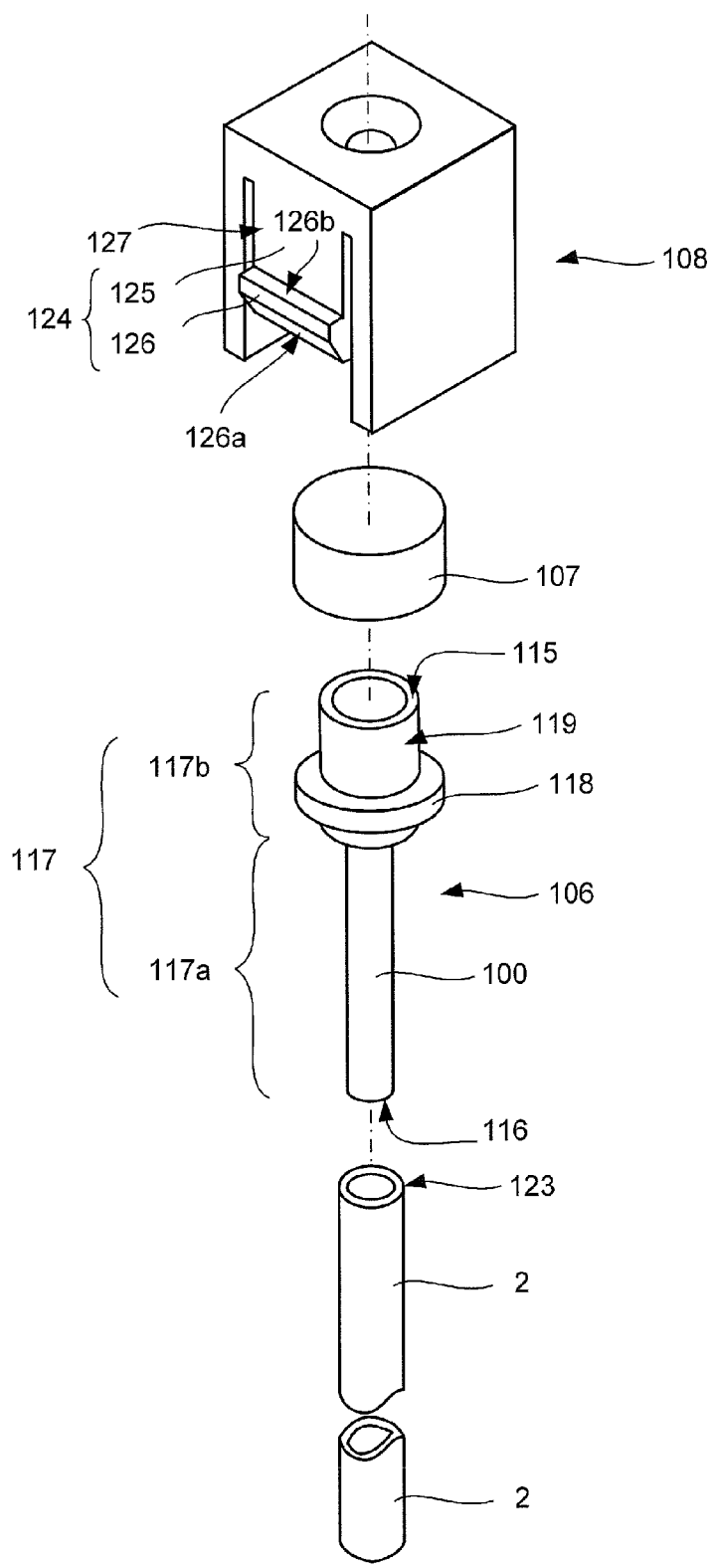
FIG. 14 is an exploded view of a septum assembly.

Referring now to FIGS. 13 and 14, the septum assembly 12 includes the soft cannula 2, a hub 106, a septum 107 and a septum cap 108. The hub 106 and the septum cap 108 are each made from plastic, such as polypropylene. The septum 107 comprises a resilient, self-sealing material, such as silicone.

In this example, the cannula 2 has a length of about 25 mm. The hub 106 has a length of about 9 mm, a maximum outer diameter of about 3 mm and an inner diameter of about 0.5 mm. The septum 107 has a diameter of about 3 mm and a thickness of the about 1.5 mm. The septum cap 108 has a length of about 5.5 mm and sides having a width of about 4 mm.

The septum cap 108 is generally box-shaped having an open front end 108a and rear end 108b. Inward facing rounded ribs 109, 110 are provided on opposite side walls 111, 112 at the front end 108a to allow snap-fit insertion of the septum 107 and the hub 106 into the cap 108. At the rear end 108b of the cap 89, a funnel-shaped (i.e. inverted frusto-conical) hole 113 which passes through an end wall 114 and through which a needle can be inserted.

The hub 106 has a first and second ends 115, 116 with a rigid tube 117 extending between the ends 115, 116. The tube 117 has two sections 117a, 117b. A first section 117a is proximate the first end 115 and has a relatively large outer diameter and second section 117b is proximate the second end 116 and has a relatively small outer diameter. The first section 117a of the tube 117 has an annular rib 118 on its outer surface 119. The first section 117a has a funnel-shaped hole 120 to help guide a needle 11 (FIG. 10) into the passageway 121 of the hub 106.

Referring in particular to FIG. 14, the first end 115 of the hub 106 presses the septum 107 against the inside face 122 of the end wall 114. The ribs 109, 110 hold the hub 106 in place by engaging an underside edge 118a of the annular rib 118. The second end 116 of the hub 106 is inserted into a proximal end 123 of the cannula 2.

The septum cap 108 includes a clip 124 comprising a deformable wing portion 125 provided by a slotted sidewall of the cap 108, and a barbed head portion 126 arranged on an outward facing surface 127 of wing portion 125. The barbed head portion 126 includes an inclined leading edge 126a and trailing edge 126b.

The head portion 126 is arranged to mate with a correspondingly-sized window 148 (FIG. 16) in the septum housing 13 (FIG. 16). The inclined leading edge 126a allows the septum assembly 12 to be inserted into the septum housing 13 (FIG. 16). Once the head portion 126 is aligned with the window 148 (FIG. 16), it is pressed through the window 148 (FIG. 16) and the trailing edge 126b is retained by a rearward edge 148a of the window 148 (FIG. 16) so as to prevent rearward displacement of the septum assembly 12 (FIG. 16) from the septum housing 13 (FIG. 16).

Referring to FIGS. 15 to 19, the septum housing 13 is moulded as a single piece and is formed from a plastics material, such as polypropylene. The septum housing 13 is generally triangular in plan view and has a low profile. The septum housing 13 is about 20 mm long and 20 mm wide and about 8 mm thick.

The septum housing 13 comprises a base portion 128 having a flat under side 129. The septum housing 13 tapers from a curved wide rear end 129, along curved sides 130, 131 to a rounded narrow front end 132. The septum housing 13 is symmetrical about a central plane 133.

At its front end 132, the septum housing 13 has a nose portion 134 upstanding from the base portion 128.

Figure 18:
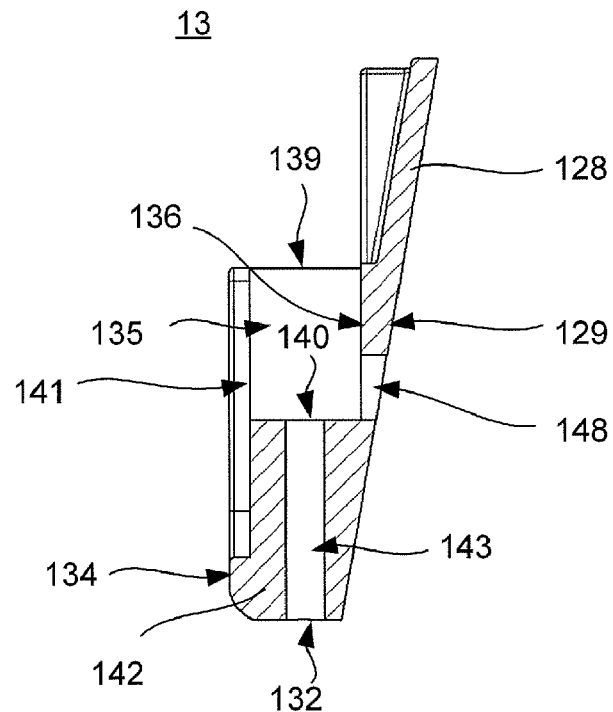
FIG. 18 is a cross sectional view of the septum housing shown in FIG. 17 taken along the line D-D'.

Referring in particular to FIGS. 15, 17, and 18, the nose portion 134 houses an elongate passage 135 for receiving the septum cap 108. The passage 135 is longitudinally arranged along about central plane 133. The passage 135 has a floor 136, sidewalls 137, 138, an open rear end 139, a front end 140 and an open top 141.

Between the front end 140 of the passage 135 and the front end 132 of the septum housing 13, the nose portion 134 includes a block 142 through which is provided a bore 143. The soft cannula 2 and the needle 11 (FIG. 10) pass through the bore 143 during insertion. The bore 143 has a diameter of about 1.5 mm.

As shown in FIG. 18, the passage 143 is inclined with respect to the flat underside 129 so as to guide the needle 11 and the cannula 2 into the surface of the skin.

The septum housing 13 includes a cover portion 144 over the nose portion 134. The cover portion 144 includes an elongate slot 145 longitudinally arranged along about central plane 133 of the septum housing 13 for receiving the spatulate member 35 (FIG. 3). The slot 145 provides the open top 141 to the passage 135 and extends over the block 142 to a rounded end 146. The slot 145 is slightly narrower than the passage 135 so as to provide a lip 147 to retain the septum cap 108.

The base portion 128 has a window 148 from the under side 129 and which opens into the passage 135 at the foot of the block 142. The window 148 is arranged to receive the clip head portion 126 (FIG. 14) of the septum assembly 12 (FIG. 14).

The nose portion 134 also houses first and second tab slots 149, 150 either side of the passage 135 for receiving the tabs 44, 45 (FIG. 3).

On a top side 151, the base portion 128 includes first and second ramps 152, 153 having upper surfaces 154, 155 inclined at substantially the same angle as passage 135 so as to help guide the cannula insertion device 3, tube connector 21 (FIG. 2e) or 'Y'-piece connector 23 (FIG. 2f) into the septum housing 13.

Referring to FIG. 17a, the nose portion 134 includes first and second retaining members 156, 157 having leading edges 158, 159, each providing a lip over which a corresponding clip heads 70, 71 (FIG. 3) can ride when the chassis 4 is inserted into the housing 13 and abrupt trailing edges 160, 161 which provide shoulders for retaining the clips 72, 73 (FIG. 3) on the cannula insertion device 3.

Figure 20:
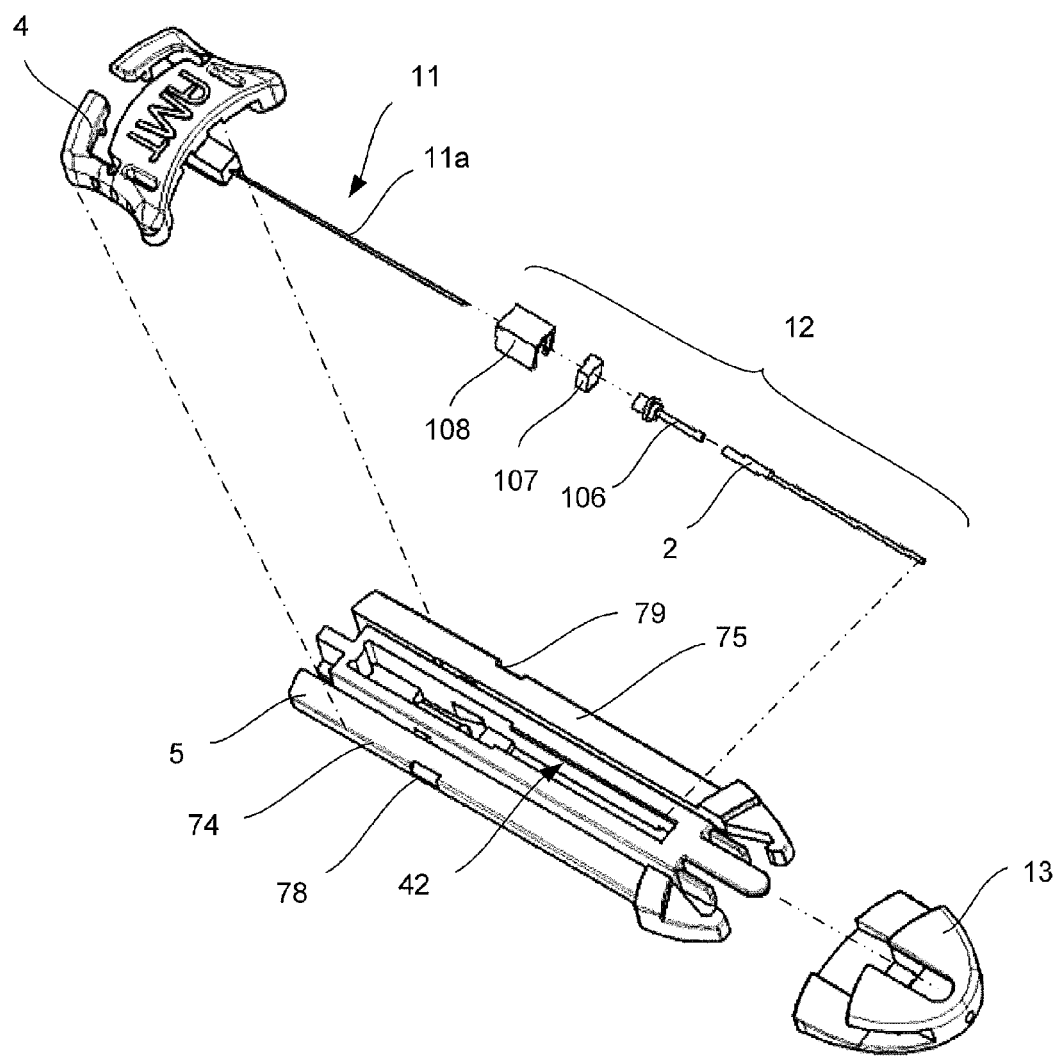
FIG. 20 is an exploded perspective view the apparatus shown in FIG. 1.

Assembly of the chassis 4, slider 5 (including needle 11), septum assembly 12 and septum housing 13 will now be described with reference to FIG. 20.

The cannula 2, hub 106, septum 107 and cap 108 are assembled and the septum assembly 12 is slid onto the shaft 11a of the needle 11. The needle 11, together with the septum assembly 12, is placed within the lumen 42 in the chassis 4 as the slider 5 is lowered onto the chassis 4 with the septum hub clip 124 (FIG. 14) facing down and with the peg 61 (FIG. 5) of the arm 49 (FIG. 4) engaging the close-ended groove 97 (FIG. 12). The slider 5 is pressed into the chassis 4 until the head portions 91a, 92a (FIG. 12) of each clip 91, 92 (FIG. 12)

rides over the chamfered portions 78, 79 and under the lips 74, 75 of the arm 26, 27 so as to hold the slider 5 and the chassis 4 together. The adhesive pad 14 (FIG. 1) is attached. The assembly 1 can now be sealed in tear open packaging (not shown), ready for use.

Figure 21A:
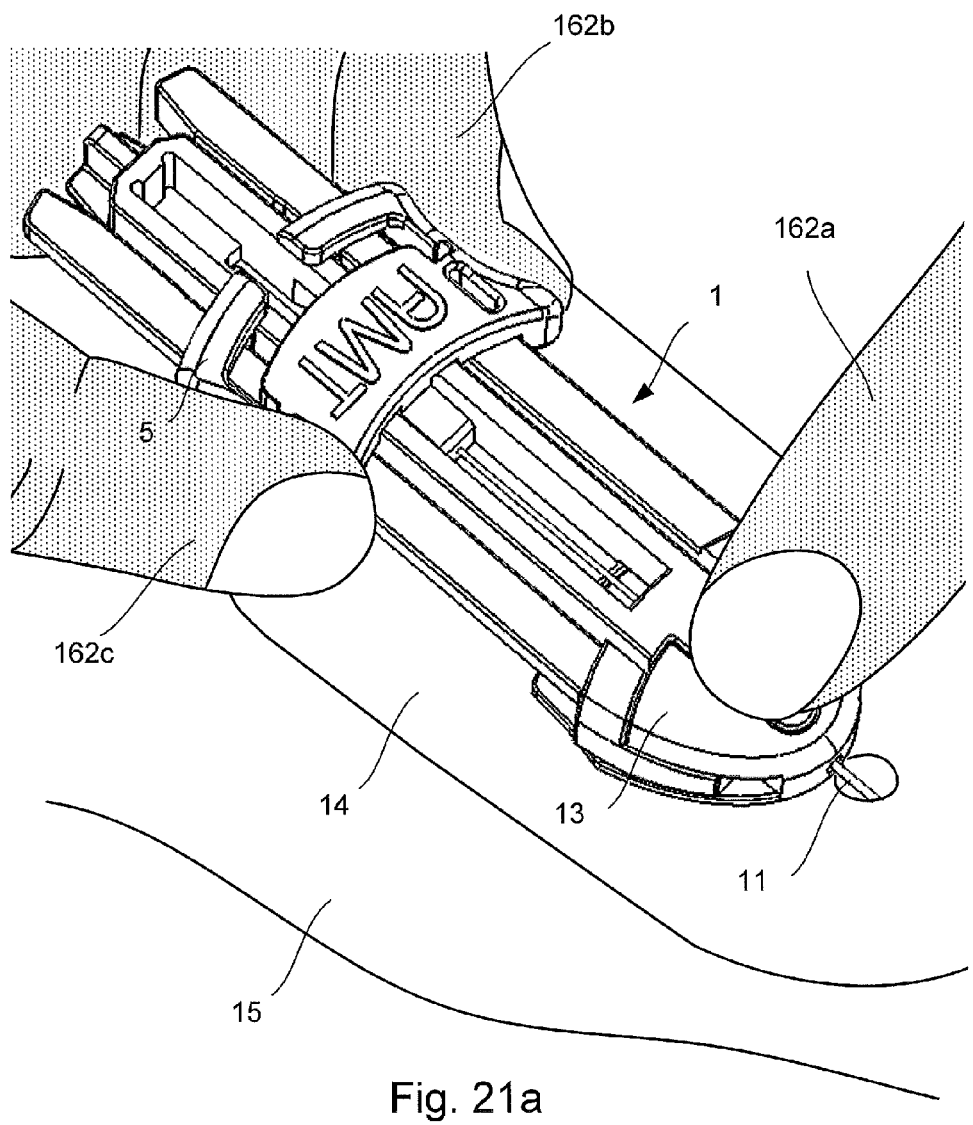
FIGS. 21a and 21b are perspective views illustrating two ways of using the assembly shown in FIG. 1.
Figure 21B:
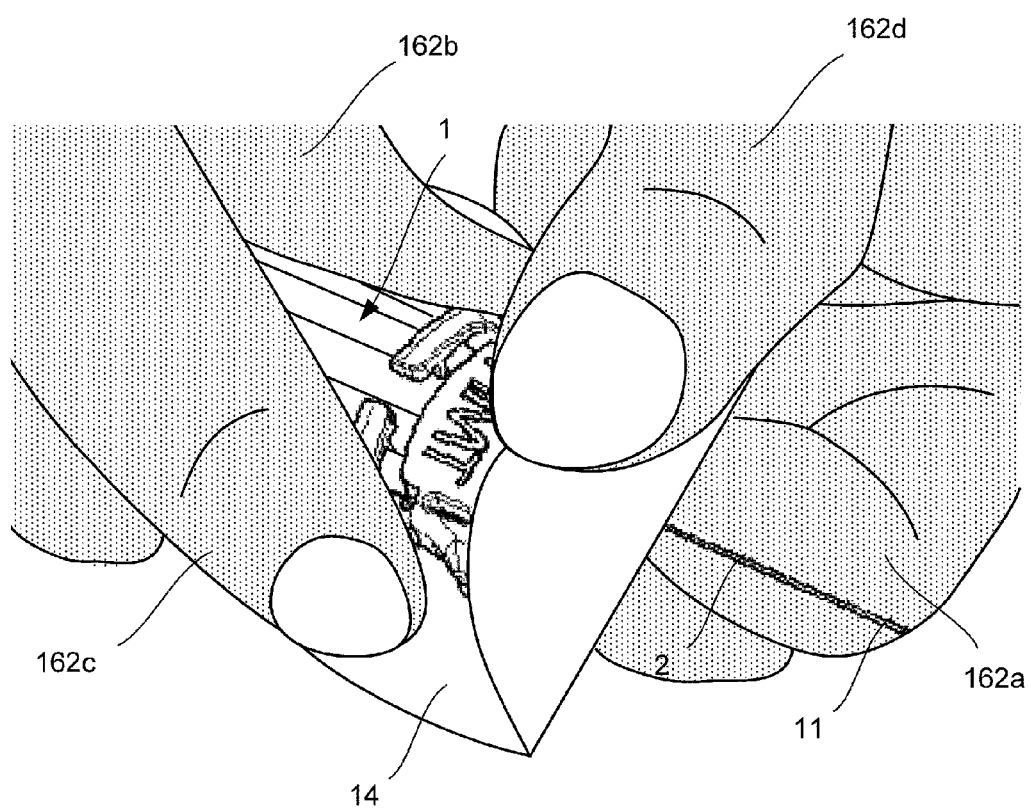

Referring to FIGS. 21a and 21b, an operator can insert the cannula 2 in one of two ways.

As shown in FIG. 21a, the operator can place and hold the septum housing 13 (with the adhesive pad 14) against the surface of the skin 15, for example using their finger(s) 162a of one hand (e.g. the left hand), and then operate the slider 5 using a thumb 162b and finger 162c of the other hand (e.g. the right hand) to extend the needle and, while doing so, also insert the needle into the patient. This approach has an advantage that it minimises possible needle-stick injury since the tip 11b (FIG. 10) of the needle 11 is exposed only briefly and only in a small space between the front of the septum housing 13 and the surface of the skin 15, which is usually only a few millimetres. This also has an advantage of helping shielding the needle 11 (FIG. 10) from the view of the patient (particularly children), who may have an aversion to needles.

Alternatively, as shown in FIG. 21b, the operator can fold back the pad 14 over the top of the septum housing 13 (not shown in FIG. 21b) so that the septum housing 13 is sandwiched by the pad 14, hold the septum housing 13 between a thumb 162d and finger 162a of one hand, and then operate the slider 5 using the thumb 162b and finger 162c of the other hand to extend, then insert the needle 11, together with the cannula 2. Notwithstanding the fact that the needle 11 is exposed while user is holding the assembly 1, the user is offered a significant degree of protection since they can extend, insert and withdraw the needle 11 while holding the assembly 1 in two hands and without needing to change their grip. This helps to significantly reduce the chances of needle stick injury.

Regardless of whether the needle 11 is inserted while it is extended or after it is extended, the user operates the assembly 1 in substantially the same way, as will now be described in more detail with reference to FIGS. 22a to 22f.

Figure 22A:
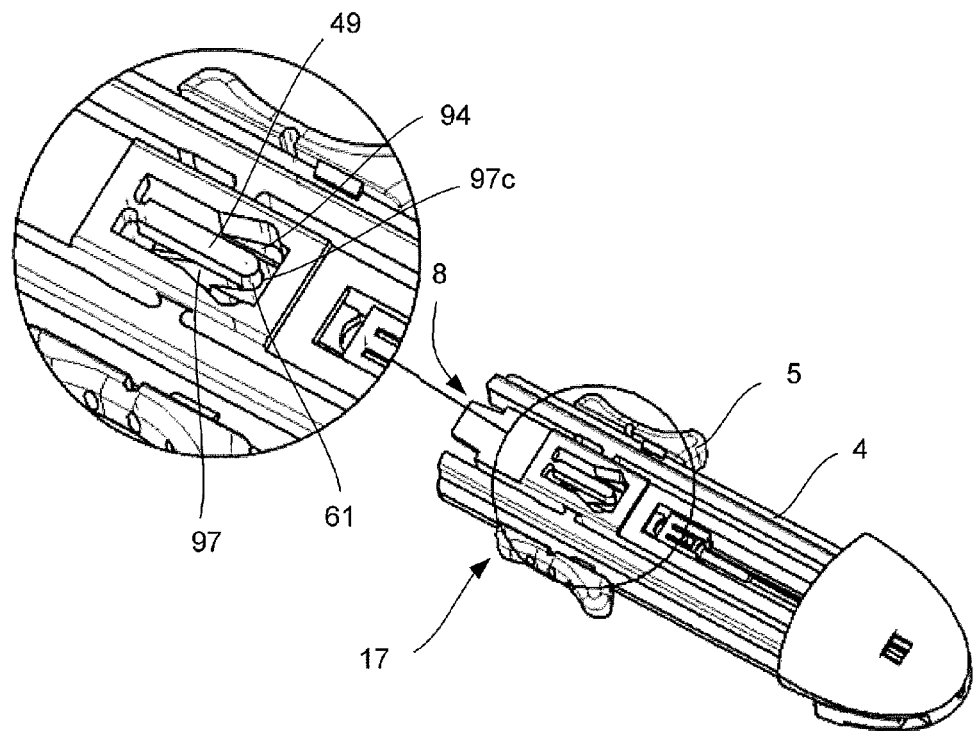
FIGS. 22a to 22g are bottom perspective views of the apparatus shown in FIG. 1 at different stages during use and include detailed views a latch arrangement.

As shown in FIG. 22a, in the ready-to-use state, the latch assembly prevents the slider 5 from being drawn back towards the second end 8 of the chassis 4. This is because the peg 61, depending from the slider 5, sits in the groove 97 and abuts the closed end 97c of the groove 97. If the operator tries to draw the slider 5 back, then the block 94 is urged backwards and presses the closed end 97c of the groove against the peg 61. If, however, the operator moves the slider 5 forwards, then the block 94 is free to move in that direction.

Figure 22B:
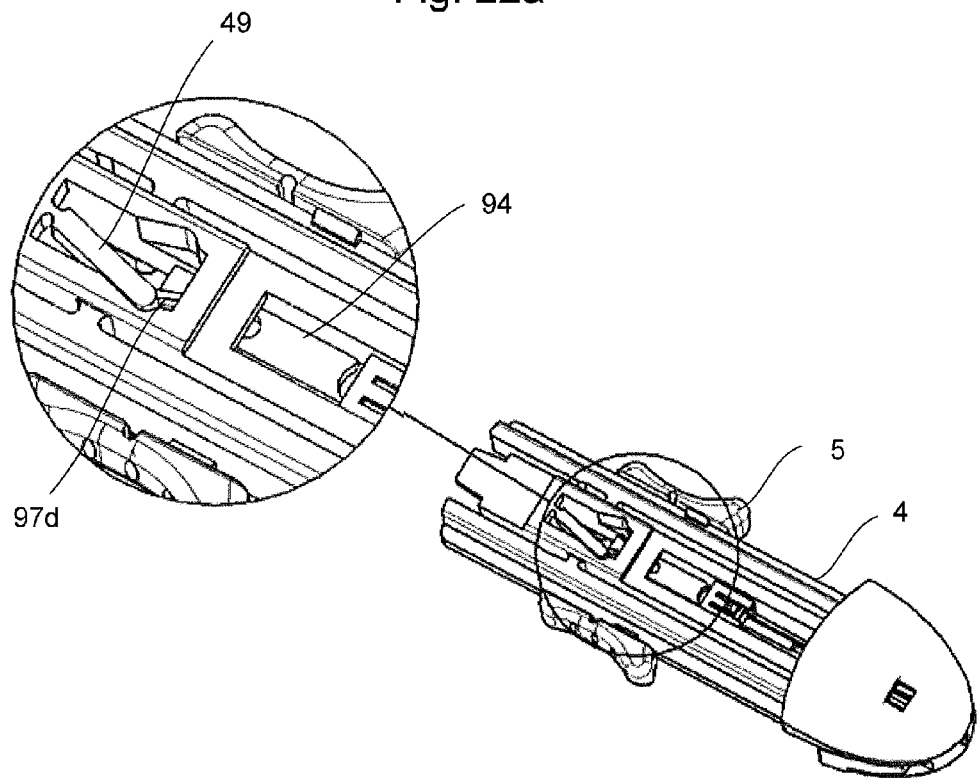

As shown in FIG. 22b, the peg 61 does not resist movement forwards. Instead, the peg 61 is guided by the groove 97 and is displaced sideways as it moves towards the open end 97d of groove 97, moving the arm 49 with it.

Figure 22C:
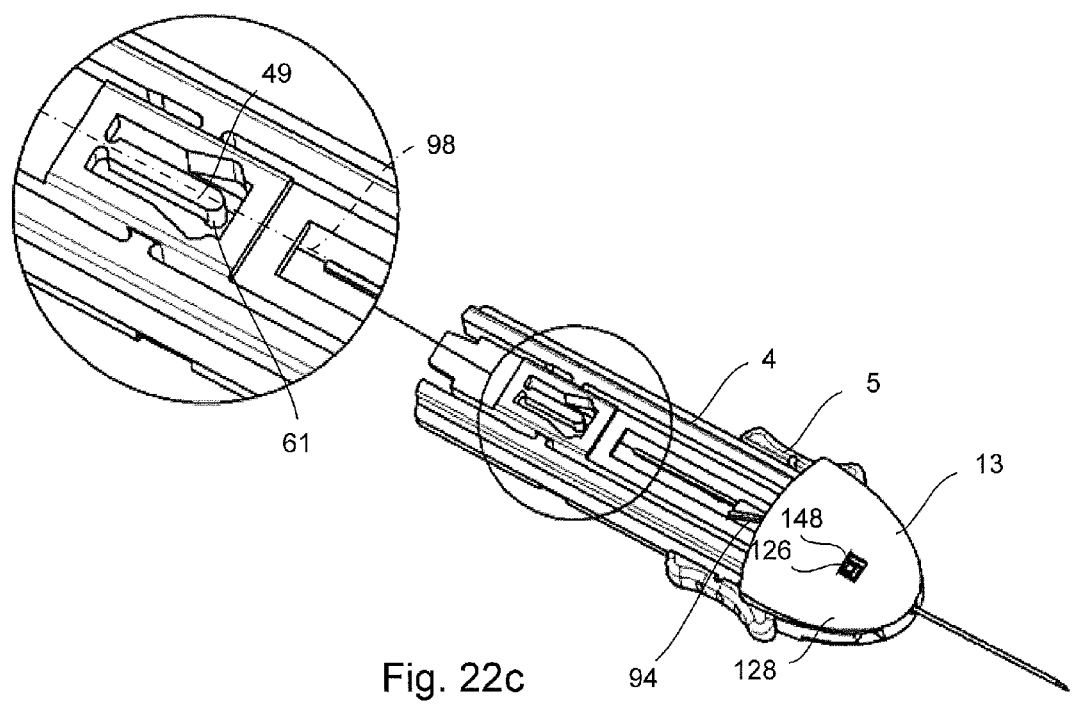

As shown in FIG. 22c, once the block 94 (FIG. 22b) clears the peg 61, the resilience of the arm 49 returns the arm 49 to its original (neutral) position pointing essentially along the axis 98 of travel. The operator moves the slider 5 forwards until the septum assembly 12 (FIG. 13) is seated in the passage 135 (FIG. 15) of septum housing 13.

Proper engagement of the septum assembly 12 (FIG. 13) in the passageway 135 (FIG. 15) is signalled to the operator by audible and/or tactual feedback, as the head portion 126 of the clip 124 of the septum assembly 12 (FIG. 14) is pressed into the window 148 in the base panel 128 of the septum housing 13 (FIG. 16).

Figure 22D:
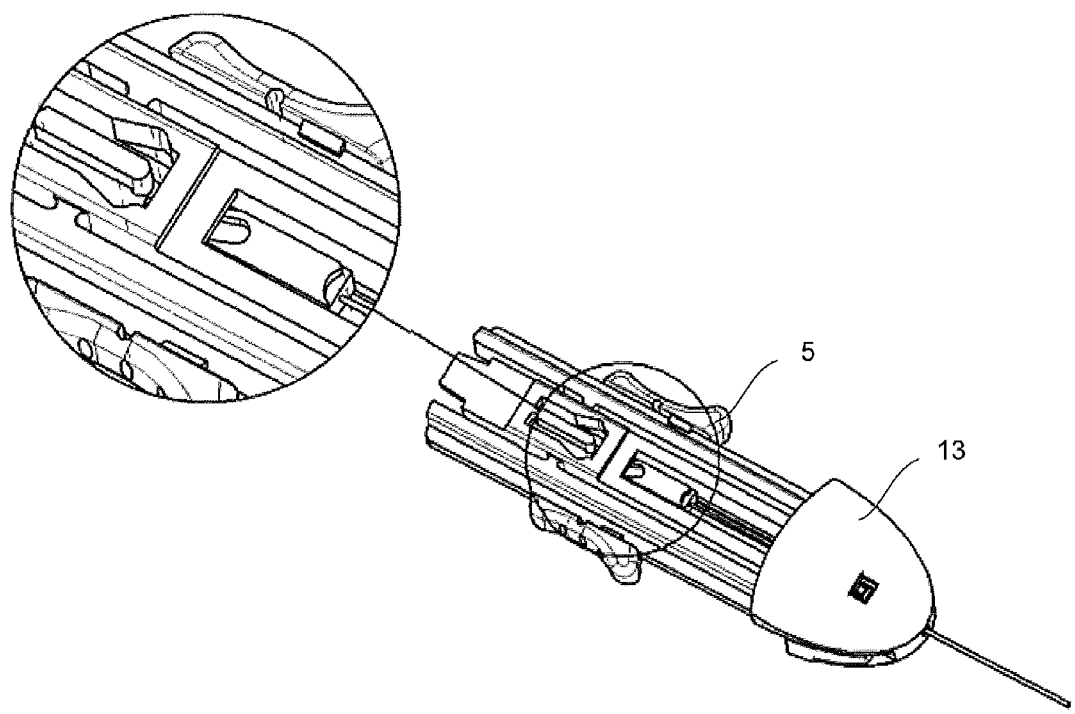

As shown in FIG. 22d, the operator can then draw back the slider 5 with the septum assembly 12 (FIG. 14) retained in the septum housing 13.

Figure 22E:
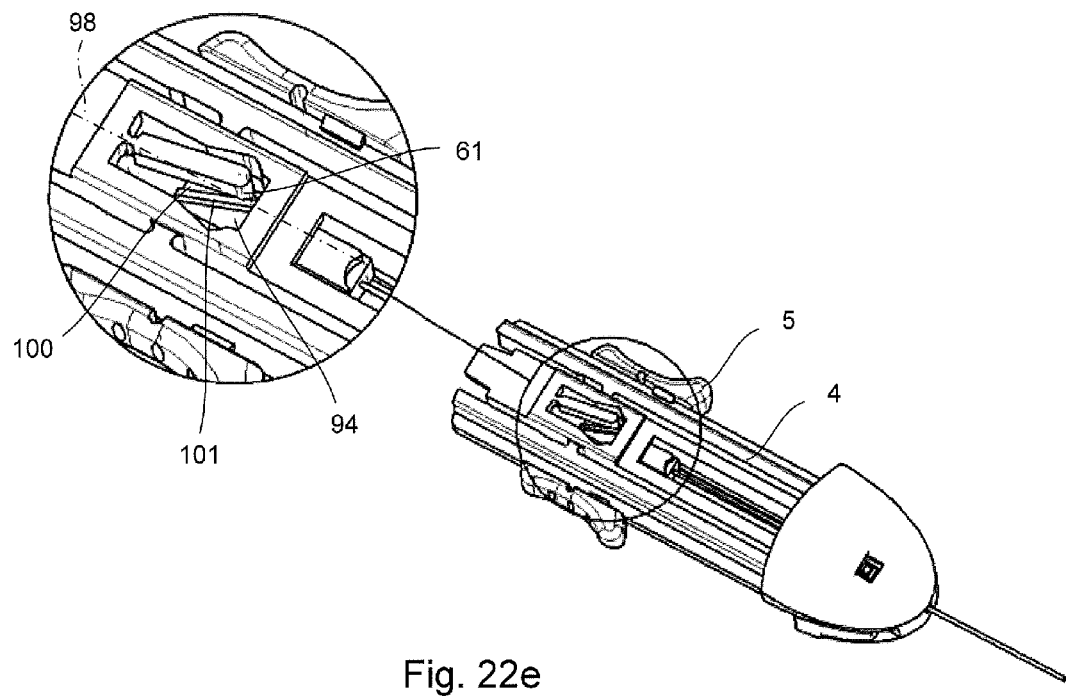

As shown in FIG. 22e, as the operator draws back the slider 5, then the block 94 is drawn back and again engages the peg 61. However, the wall 101 lies across the axis 98 of travel and so the peg 61 is urged to into the open-sided recess 100, i.e. the peg 61 is not channelled down the closed-ended groove 97. This allows the slider 5 to be drawn back beyond the first position 17 (FIG. 2d).

Figure 22F:
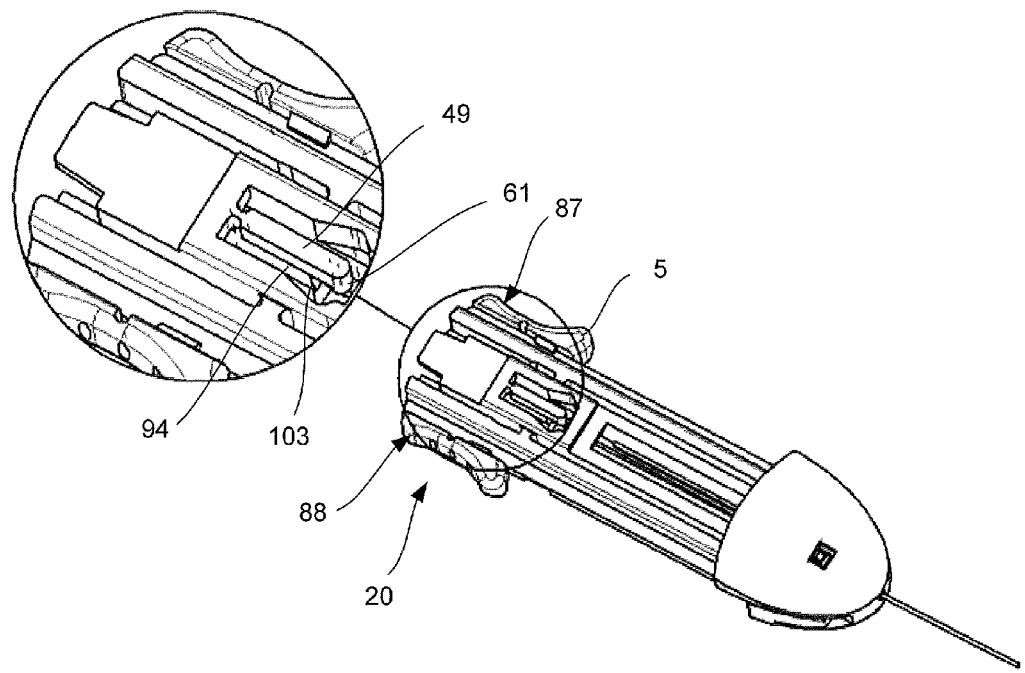

As shown in FIG. 22f, once the block 94 clears the peg 61, the resilience of the arm 49 returns the arm 49 to its a neutral position. Drawing back of the slider 5 can continue until the slider 5 reaches the end of the chassis 4, stopped when the block 94 hits the face 37a (FIG. 5) of the stem 37 (FIG. 5). However, forward movement of the slider 5 is now prevented by the detent 103 urging against the peg 61.

The slider 5 is now in the third position 20 in which the used needle 11 is safely stored.

Figure 22G:
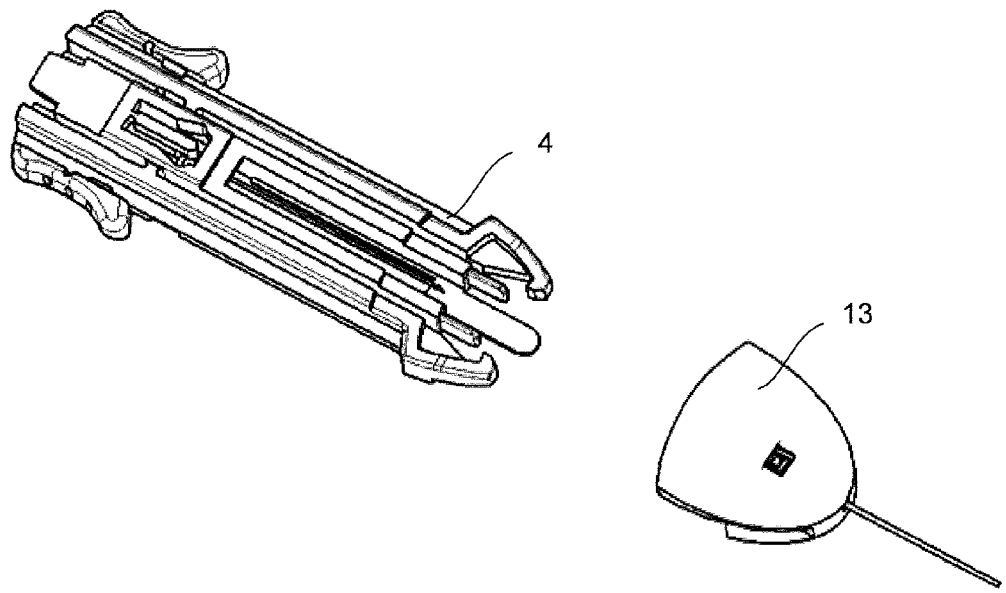

Referring to FIGS. 3, 11 and 22g, in the third position 20, the user can now detach the insertion device 3 from the septum housing 13. The fins 89, 90 have passed beyond the outward facing sides 28, 29 of central body 25. Thus, there is no surface stopping the fins 89, 90. Therefore, by continuing to press or by applying additional pressure to the surfaces gripping surfaces 87, 88, the user is able to bring the posterior distal ends 66, 67 of the arms 26, 27 closer together, causing the arms 26, 27 to pivot and so widen the gap between the anterior distal ends 68, 69 (FIG. 3) of the arms 26, 27. This causes the heads 70, 71 of the clips 72, 73 of the chassis 4 to clear the retaining members 156, 157 (FIG. 17a) in the septum housing 13 thereby allowing the chassis 4 to be withdrawn and disengaged from the septum housing 13, as shown in FIG. 22h.

The septum housing 13 is now ready for tube connector 21 (FIG. 2e) or 'Y'-piece connector 23 (FIG. 2f) to be coupled on so as to deliver a fluid to the patient, such as a drug or combination of drugs.

Figure 23:
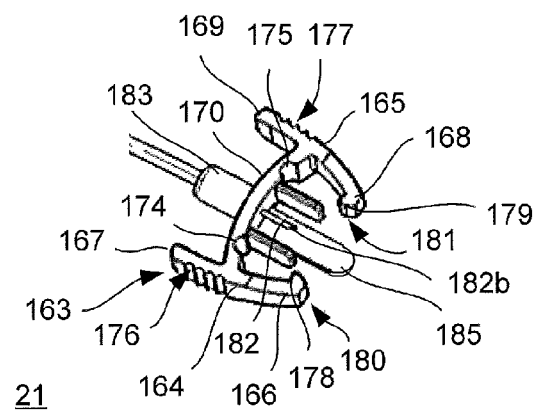
FIGS. 23 and 23a are bottom perspective views of a tube connector.
Figure 24:
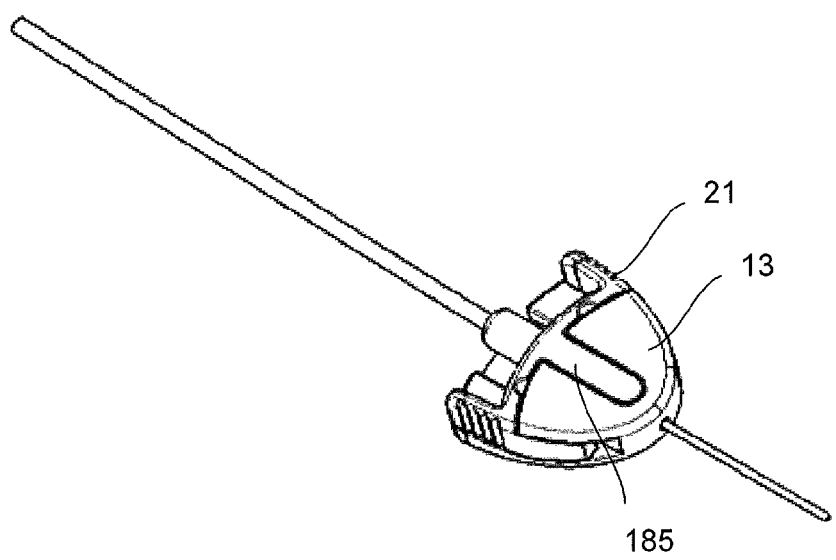
FIG. 24 is a top perspective view of the tube connector and septum housing when connected.

Referring to FIGS. 23 and 24, the tube connector 21 is formed from a plastic material, such as polypropylene. The tube connector 21 is generally flat and 'H'-shaped in plan view. In this example, the tube connector 21 has a length of about 19 mm, a width of about 21 mm and a thickness of about 5 mm.

The tube connector 21 comprises a base portion 163 having first and second arms 164, 165. The arms 164, 165 each have first and second ends 166, 167, 168, 169 and are generally arranged in parallel. A crosspiece 170 connects the arms 164, 165 on inward facing sides approximately midway between first and second ends 166, 167, 168, 169, thereby forming an 'H'-shaped structure.

The crosspiece 170 is provided with first and second notches 174, 175 so as to allow the crosspiece to flex. Outward facing surfaces 176, 177 of the arms proximate the rear ends 167, 169 provide first and second opposing surfaces for gripping between a finger and thumb. The surfaces are ribbed so as to improve grip.

The forward distal ends 166, 168 of the arms 164, 165 each have inwardly facing barbed heads 178, 179 to provide clips 180, 181 for co-operating with clip retaining members 156, 157 (FIG. 17a) in the septum housing 13. The clips 180, 181 are substantially the same as the clips 72, 73 on the insertion device 3, thereby allowing the tube connector 21 to be interchanged with insertion device 3.

A hollow needle 182 projects forwardly from the crosspiece 170. The needle 182 has a shaft and a tip and has an exposed length of about 4 mm. A tubular port 183 projects rearward from the crosspiece 170. The needle 182 and the port 183 are in fluid communication via a bore (not shown).

A spatulate member 185 projects forwardly from the crosspiece 170 parallel to the needle and fully facing the shaft 182b of the needle 182.

The spatulate member 185 is substantially the same in form and dimensions as the spatulate member 35 (FIG. 3) on the chassis 4 (FIG. 3) and has substantially the same arrangement relative to the clips 180, 181 as the spatulate member 35 (FIG. 3) has relative to the clips 72, 73 (FIG. 3) on the chassis 4 (FIG. 3), thereby allowing the tube connector 21 to replace the insertion device 3 (FIG. 2d).

Figure 23A:
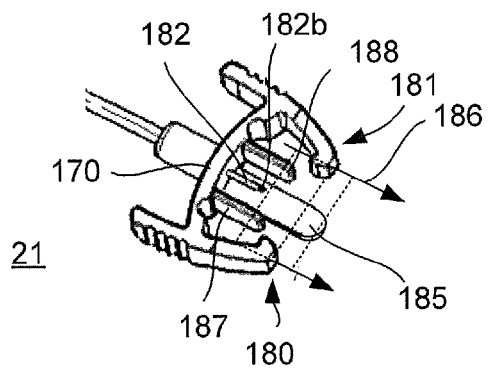

Referring in particular to FIG. 23a, the spatulate member 185 arranged to extend beyond the tip 182b of the needle 182 and further arranged so as to be furthest extent of the tube connector 21 in the forward direction 186. Thus, the spatulate member 185 allows the connector 21 to be orientated and guided into the septum housing 13 before the clips 180, 181 engage the retaining members.

Tabs 187, 188 which are flat and narrow in section project forwardly from crosspiece 170 to provide lateral guards to shield the needle 182.

FIG. 24 shows the tube connector 21 coupled to the septum housing 13. The tube connector 21 may be repeatedly coupled and de-coupled. This allows the patient to be disconnected from the drug delivery device, usually temporarily, so as to allow freedom of movement. The tube connector 21 may be swapped for a different tube connector 21.

Figure 25:
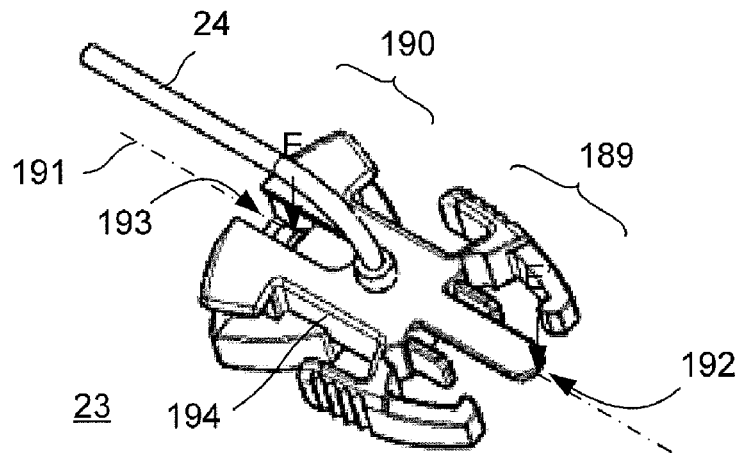
FIG. 25 is a top perspective view of a 'Y'-piece connector and a septum housing.
Figure 26:
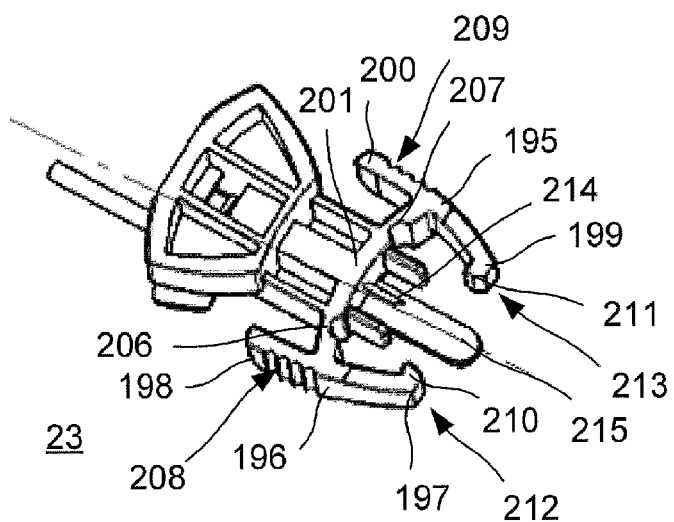
FIGS. 26 and 26a are bottom perspective views of a 'Y'-piece connector and a septum housing.

Referring to FIGS. 25 and 26, the 'Y'-piece tube connector 23 is formed from a plastic material, such as polypropylene.

The 'Y'-piece tube connector 23 has forward and rear sections 189, 190 arranged in line along a longitudinal axis 191 between forward and rear ends 192, 193 and joined by a bridge portion 194.

The forward section 189 has a configuration similar to the tube connector 21 (FIG. 23) hereinbefore described. The rear section 190 has a configuration similar to the nose section portion 134 (FIG. 15) of the septum housing 13 hereinbefore described.

The forward section 189 has first and second arms 195, 196. The arms 195, 196 each have first and second ends 197, 198, 199, 200 and are generally arranged in parallel. A crosspiece 201 connects the arms 195, 196 on inward facing sides at approximately midway between first and second ends 197, 198, 199, 200, thereby forming an 'H'-shaped structure.

The crosspiece 201 is provided with thinned sections 206, 207 using notches so as to allow the crosspiece 201 to flex. Outward facing surfaces 208, 209 of the arms 195, 196 proximate the rear ends 198, 200 provide first and second opposing surfaces for gripping between a finger and thumb. The surfaces 208, 209 are ribbed so as to improve grip.

The forward distal ends 197, 199 of the arms 195, 196 each have inwardly facing barbed heads 210, 211 to provide clips 212, 213 for co-operating with clip retaining members 156, 157 (FIG. 19) in the septum housing 13. The clips 212, 213 are substantially the same as the clips 72, 73 (FIG. 5) on the chassis 4 (FIG. 5) and the clips 180, 181 (FIG. 23) on the tube connector 21 (FIG. 23) so as to allow the tube 'Y'-piece tube connector 23 and the tube connector 21 (FIG. 23) to be interchanged.

A hollow needle 214 projects forwardly from the crosspiece 201. The needle 214 has a shaft 214a and a tip 214b and has an exposed length of about 4 mm.

A spatulate member 215 projects forwardly from the crosspiece 201 parallel to the needle and facing fully the shaft 214b of the needle 214.

The spatulate member 215 is substantially the same in form and dimensions as the spatulate member 35 on the insertion device 3 and has substantially the same arrangement relative to the clips 212, 213 as the spatulate member 35 has relative to the clips 72, 73 (FIG. 5) on the insertion device 3 (FIG. 1), thereby allowing the 'Y'-piece tube connector 23 to replace the insertion device 3 (FIG. 1).

Figure 26A:
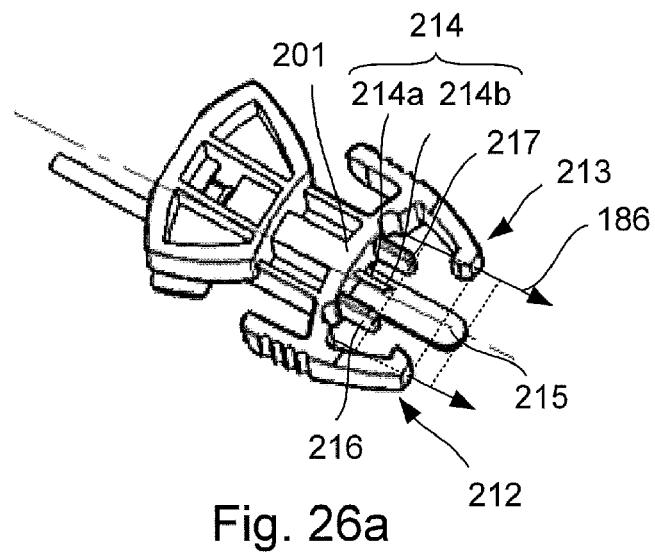

Referring in particular to FIG. 26a, the spatulate member 215 arranged to extend beyond the tip 214b of the needle 214 and further arranged so as to be furthest extent of the 'Y'-piece tube connector 23 in a forward direction 216. Thus, the spatulate member 215 allows the 'Y'-piece tube connector 23 to be orientated and guided into the septum housing 13 (FIG. 15) before the clips 212, 213 engage the retaining members 156, 157 (FIG. 17a).

Tabs 216, 217 which are flat and narrow in section project forwardly from crosspiece 201 to provide lateral guards to shield the needle 214.

Figure 27:
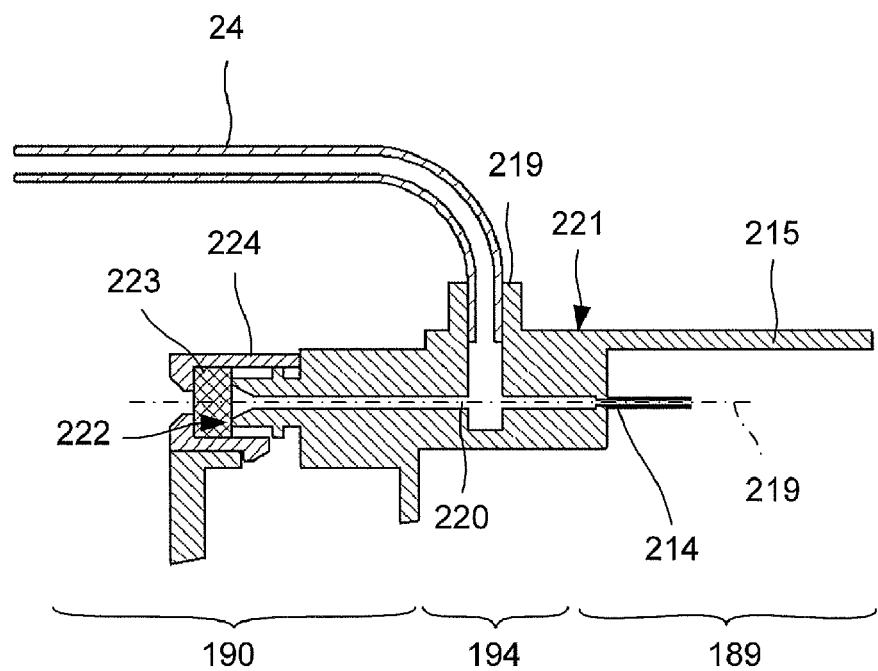
FIG. 27 is a cross-sectional view of the 'Y'-piece connector taken along the line F-F'.

Referring to FIG. 27, the bridge portion 194 includes a port 219 which feeds into a bore 220 providing fluid communication between forward and rear sections 189, 190. The port 219 is provided on an upper side 221 and has a flexible tube 24 bonded to it.

The port 219 may exit substantially perpendicular to the bore 220 on the upper side, as shown in FIG. 27. However, the port 219 may be provided on a lower side (i.e. skin side). This can help to minimise the profile of the connector 23 and help avoid the tube 24 being caught or snagged. The port 219 may have an 'L'-shaped bend so that it exits substantially parallel to the bore 20 directed towards the rear of the connector 23. This can also help to minimise the profile of the connector 23.

The rear end 222 of the bore 220 is capped off by a septum 223 held in place by a cap 224. The cap 224 is similar to the septum cap 208 (FIG. 14) and snaps fits into the rear section 190 of the 'Y'-piece tube connector 23 in a similar way to that described earlier.

When a tube connector 21 (FIG. 23) is inserted into the rear section of the 'Y'-piece connector 23, the needle 182 (FIG. 23) of the tube connector 21 (FIG. 23) pierces the septum 223.

Figure 28:
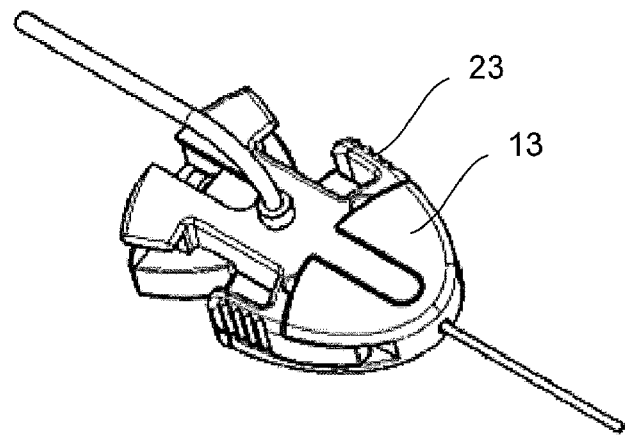
FIG. 28 is a top perspective view of a 'Y'-piece connector and a septum housing when connected.

FIG. 28 shows the 'Y'-piece tube connector 23 coupled to the septum housing 13. Similar to the tube connector 21 (FIG. 24) described earlier, the Y'-piece tube connector 23 may be repeatedly coupled and de-coupled and/or be swapped for a different tube connector 21.

Figure 29:
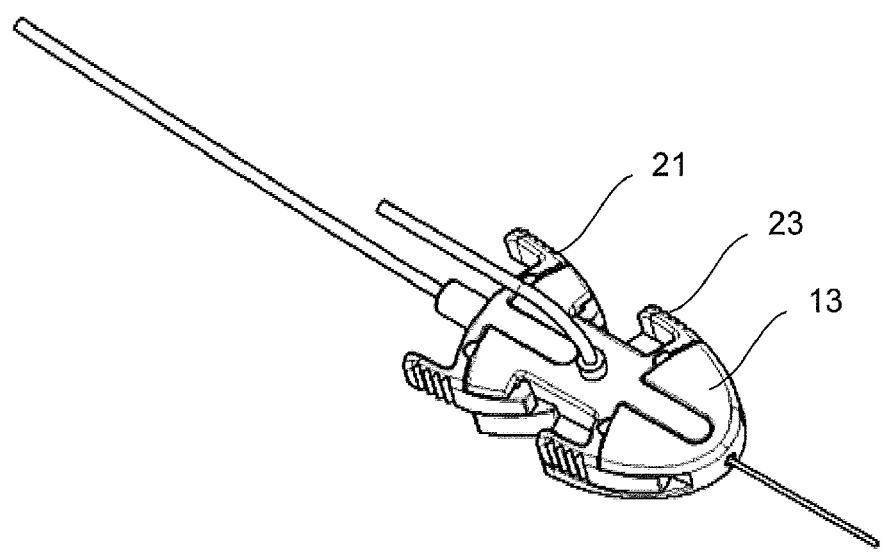
FIG. 29 is a top perspective view of a tube connector, 'Y'-piece connector and a septum housing when connected together.

FIG. 29 shows a tube connector 21 coupled to the 'Y'-piece tube connector 23 which in turn is coupled to the septum housing 13. Thus, using the 'Y'-piece tube connector 23 allows two fluids from different supply devices to be delivered via the same access site, i.e. via the same cannula.

It will be evident to those skilled in the art that various other modifications to the form, details and dimensions of the assembly may be made within the scope of the invention.

While the invention has been described in relation to placing a cannula for administering a drug subcutaneously, it will be appreciated that the assembly can be used or modified, for example by elongating the cannula, chassis and the needle, for administering a drug intravenously, for example into the central line.

The invention claimed is:

1. An apparatus comprising:
 a cannula insertion device comprising:
  a frame;
  a hub mounted to the frame and arranged to be slidably moveable from a first position in a first direction to a second position relative to the frame; and
  a needle projecting in the first direction from the hub, the needle being shielded by the frame when the hub is in the first position; and
 a detachable cannula assembly including a cannula, the needle carrying the detachable cannula assembly;

the frame and hub arranged to allow the hub to be moved from the first position to the second position so as to insert the cannula into a patient and to be moved in a second, reverse direction backwards to a third position in which the frame shields the needle;

the apparatus further comprising:

a housing for receiving the detachable cannula assembly, wherein the cannula insertion device is removeably attached to the housing and is detachable from the housing only once the hub is in the third position, wherein the frame includes first and second arms running along opposite sides of a central portion of the frame and attached thereto by respective deformable hinges, each arm having an anterior distal end and a posterior distal end relative to the hinge of the arm, the anterior distal ends of the arms arranged to provide jaws for releasably attaching the cannula insertion device to the housing for receiving the detachable cannula assembly; and wherein the hub has opposing surfaces for gripping between a finger and thumb of one hand and which lie outside the arms of the frame, at least a portion of the hub being deformable so as to allow the opposing surfaces to be moved inwards when pressed together.

2. The apparatus according to claim 1, wherein the frame is elongate and the hub is slidably moveable along the longitudinal axis of the frame.

3. The apparatus according to claim 1, wherein the frame and hub are further arranged to provide a latch so as to lock the hub in the third position so as to prevent the hub being moved forward.

4. The apparatus according to claim 1, wherein the frame includes first and second beams running adjacently between first and second ends, the hub and frame arranged such that the needle sits between the beams.

5. The apparatus according to claim 4, wherein the frame includes a cover spanning the beams and running between the first and second ends so as to define a space in which the needle sits.

6. The apparatus according to claim 4, wherein the first and second beams include respective lip portions partially spanning the beams and running between the first and second ends so as to define slot along the frame.

7. The apparatus according to claim 1, wherein the hub includes first and second arms disposed on either side of a central portion, said opposing surfaces being outer surfaces of the first and second arms.

8. The apparatus according to claim 1, wherein the frame is arranged such that when the hub is substantially in the third position and the opposing surfaces are pressed together, the posterior distal ends of the arms of the frame are pressed inwards and the anterior distal ends of the arms of the frame move outwards away from the central portion.

9. The apparatus according to claim 1, wherein the frame and hub are provided with cooperating surfaces such that when the hub is in a position which allows the posterior distal ends of the arms of the frame to be pressed inwards, the cooperating surfaces resist inward movement of the posterior distal ends of the arms of the frame and thus prevent outward movement of anterior distal ends of the arms of the frame away from the central portion.

10. The apparatus according to claim 9, wherein the cooperating surface of the frame comprises outward facing sides of the central portion.

11. The apparatus according to claim 9, wherein the cooperating surface of the hub comprises upstanding fins.

12. The apparatus according to claim 1, wherein the frame and hub are arranged such that when the hub is between the first and second positions and when the opposing surfaces of the hub are pressed together, anterior distal ends of the arms are pressed towards the central portion.

13. A method of inserting a cannula using apparatus comprising a cannula insertion device comprising a frame, a hub mounted to the frame and arranged to be slidably movable in a first direction from a first position to a second position relative to the frame and a needle projecting in the first direction from the hub along the longitudinal axis and carrying a detachable cannula assembly including a cannula, the needle being shielded by the frame when the hub is in the first position, the apparatus further comprising a housing for receiving the detachable cannula assembly, wherein the cannula insertion device is removeably attached to the housing and is detachable from the housing only once the hub is in a third position, wherein the frame includes first and second arms running along opposite sides of a central portion of the frame and attached thereto by respective deformable hinges, each arm having an anterior distal end and a posterior distal end relative to the hinge of the arm, the anterior distal ends of the arms arranged to provide jaws for releasably attaching the cannula insertion device to the housing for receiving the detachable cannula assembly; and wherein the hub has opposing surfaces for gripping between a finger and thumb of one hand and which lie outside the arms of the frame, at least a portion of the hub being deformable so as to allow the opposing surfaces to be moved inwards when pressed together, the method comprising:

gripping the opposing surfaces of the hub between a finger and thumb of one hand;

moving the hub in the first direction from the first position to the second position so as to insert the cannula into a patient;

drawing the hub in a second, reverse direction to the third position in which the frame shields the needle; and detaching the cannula insertion device from the housing when the hub is in the third position.

* * * * *